(12) United States Patent
Zupkas et al.

(10) Patent No.: US 8,741,330 B2
(45) Date of Patent: Jun. 3, 2014

(54) TRANSLUMINAL DRUG DELIVERY METHODS AND DEVICES

(76) Inventors: Paul Zupkas, San Diego, CA (US); C. Lowell Parsons, San Diego, CA (US)

( * ) Notice: Subject to any disclaimer, the term of this patent is extended or adjusted under 35 U.S.C. 154(b) by 0 days.

(21) Appl. No.: 13/619,324

(22) Filed: Sep. 14, 2012

(65) Prior Publication Data

US 2013/0071445 A1    Mar. 21, 2013

Related U.S. Application Data

(63) Continuation of application No. 11/475,809, filed on Jun. 26, 2006, now abandoned, which is a continuation-in-part of application No. 11/340,071, filed on Jan. 26, 2006, now abandoned.

(51) Int. Cl.
  *A61F 6/06*    (2006.01)
  *A61F 13/00*   (2006.01)
  *A61K 9/02*    (2006.01)

(52) U.S. Cl.
  CPC ........................................ *A61K 9/02* (2013.01)
  USPC .......................................... 424/430; 424/433

(58) Field of Classification Search
  CPC ....................................................... A61K 9/02
  See application file for complete search history.

(56) References Cited

U.S. PATENT DOCUMENTS 4,789,669 A * 12/1988 Sugimoto et al. ............. 514/178
2004/0209869 A1* 10/2004 Landau et al. ................ 514/218

FOREIGN PATENT DOCUMENTS

WO    WO 2005072751 A1 *  8/2005

* cited by examiner

*Primary Examiner* — Susan Tran
(74) *Attorney, Agent, or Firm* — Ditthavong Mori & Steiner, P.C.

(57) ABSTRACT

Transluminal drug delivery method and device embodiments can include a urethral suppository formulated to prevent or treat diseases of the urethra and surrounding organs, such as interstitial cystitis or urethritis, by enhancing the absorption of a therapeutic agent of the suppository into body tissues without adversely affecting the natural defense mechanisms of these tissues. Adverse effects on the glycosaminoglycan (GAG) barrier can be mitigated or eliminated by the presence of a suitable polysaccharide in the suppository.

36 Claims, 19 Drawing Sheets

TRANSLUMINAL DRUG DELIVERY METHODS AND DEVICES

CROSS-REFERENCE TO RELATED APPLICATIONS

This application is a continuation application of U.S. patent application Ser. No. 11/475,809, filed Jun. 26, 2006, which is a continuation-in-part application of U.S. patent application Ser. No. 11/340,071 by Zupkas et al., entitled "Transluminal Drug Delivery Methods and Devices," filed on Jan. 26, 2006, the entireties of which are incorporated herein by reference.

BACKGROUND OF THE INVENTION

Diseases of the urinary tract present a growing healthcare problem worldwide. One of the most common diseases of the urinary tract is interstitial cystitis. Interstitial cystitis (IC) is a clinical syndrome of frequency, urgency, and/or pelvic pain in the absence of any definable pathology, such as urinary infection, carcinoma, or cystitis induced by radiation or medication. A diagnosis of IC is often reached as a diagnosis of exclusion, where patients have tried treatments for other diseases exhibiting similar symptoms and those treatments have failed to alleviate the symptoms. The disease is best understood as a continuum, with an early phase in which symptoms are intermittent, a middle phase in which symptoms may be chronic and flare episodically, and sometimes a late phase in which bladder destruction occurs. In its early stages, IC is often mistaken for other urologic or gynecologic disorders, and tends to go unrecognized until its advanced stages. Treatment options for IC are limited. There are few oral or intravesical medications that have shown efficacy in treating IC. Physical intervention in the form of a cystectomy is used as a last resort in end stage disease. Although IC was traditionally diagnosed almost exclusively in women, the number of men diagnosed with IC has been increasing as well.

Although oral medications, such as pentosanpolysulfate (Elmiron®) and hyaluronic acid, are used to treat IC by replacing missing components in a defective glycosaminoglycan (GAG) barrier, a fundamental characteristic of IC, the use of oral anesthetic agents to inhibit urinary tract sensory nerve activation is impractical. Oral drug delivery affects the entire body, requiring high oral doses of drugs to achieve therapeutically significant levels in a target organ. When the organ is in the urinary tract, such as the bladder or urethra, oral drugs must pass through and be affected by other organs before reaching their target. This effect may change the activity or function of the drug resulting in undesirable side effects or other co-morbidities. An alternative to oral delivery is topical or site-specific delivery of the drug, where the drug is delivered directly to the diseased organ. Topical drug delivery generally provides similar efficacy at lower drug doses than oral delivery, and may reduce or eliminate the effect of the drug on any other organs than the target organ.

The use of urethral suppositories for topical drug delivery has been known. However, existing modalities do not allow for an efficient absorption of some beneficial therapeutic agents. What have been needed are systems and methods for efficient delivery of therapeutic agents to at least a portion of the tissue of a patient's urinary tract, or surrounding tissue thereof.

SUMMARY OF THE INVENTION

Some embodiments of a urethral suppository include a carrier base material, an anesthetic agent, and a buffering agent formed into a solid structure configured for insertion into a patient's urethra. Such embodiments can include a polysaccharide and can be prepared as a substantially uniform composition. The carrier base material can have a melting point such that the suppository is substantially melted at body temperature. Alternatively, the carrier base material can be a water soluble carrier base. Typically, the carrier base material is at least one material selected from the group consisting of paraffin, theobroma oil, modified theobroma oil products, gelatins, glycerinated gelatins, polyethylene glycols (PEGs), glycerols, hydrogenated vegetable oils, cocoa butter, methyl butyl ketone (MBK), celluloses, polyvinyl alcohol, polyvinylpyrrolidone, polyacrylamide, polyphosphourethanes, polyoxyl stearate, ethylene oxide polymers, and fatty acid bases. A preferred carrier base material is methyl butyl ketone, which can further include paraffin. If a polysaccharide is present, it is typically present in the suppository in a sufficient quantity to prevent or ameliorate a urinary tract disorder. The urinary tract disorder can be, but is not limited to, interstitial cystitis (IC) or urethritis. Typically, the polysaccharide is at least one polysaccharide selected from the group consisting of hyaluronic acid, hyaluronan, chondroitin sulfate, pentosan polysulfate, dermatan sulfates, heparin, heparan sulfates, keratan sulfates, dextran sulfates, and carrageenan. A particularly preferred polysaccharide is heparin.

Typically, the therapeutic agent is an anesthetic agent. Typically, the anesthetic agent is present in a quantity sufficient to prevent or ameliorate a urinary tract disorder. Typically, the anesthetic agent is at least one anesthetic agent selected from the group consisting of lidocaine, benzocaine, bupivacaine, articaine, cocaine, etidocaine, flecamide, mepivacaine, pramoxine, prilocalne, procaine, chloroprocaine, oxyprocaine, proparacaine, ropivacaine, tetracaine, dyclonine, dibucaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof, as well as combinations thereof. A preferred anesthetic agent is lidocaine.

Typically, the buffering agent is present in a quantity such that the buffering agent buffers the suppository at a pH that ensures that a sufficient portion of an anesthetic agent that is present in the suppository is present in an uncharged state so that the anesthetic agent can cross cell membranes of cells surrounding the urethra. Typically, the buffering agent maintains the pH of the suppository in a range of from about 7 to about 12; more typically, the buffering agent maintains the pH of the suppository in a range of from about 7 to about 9. Typically, the buffering agent is at least one buffer selected from the group consisting of sodium bicarbonate buffer, calcium bicarbonate buffer, tris(hydroxymethyl)aminomethane (Tris or THAM), MOPS (3-(N-morpholino)propanesulfonic acid) buffer, HEPES (N-(2-hydroxyethyl)piperazine-N'-(2-ethanesulfonic acid) buffer, ACES (2-[(2-amino-2-oxoethyl)amino]ethanesulfonic acid) buffer, ADA (N-(2-acetamido)-2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino) ethanesulfonic acid) buffer, DIPSO (3-[N,N-bis(2-hydroxyethyl)amino]-2-hydroxy-propanesulfonic acid) buffer, HEPPS(N-(2-hydroxyethylpiperazine)-N'-(3-propanesulfonic acid), buffer, HEPPSO (N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropanesulfonic acid) buffer; TAPS (N-tris[hydroxymethyl)methyl-3-aminopropanesulfonic acid) buffer, TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer, as well as combinations thereof. Particularly preferred buffering agents include sodium bicarbonate buffer and tris(hydroxymethyl)aminomethane buffer.

Typically, the suppository is from about 10 mg to about 1000 mg in weight; more typically, from about 400 mg to about 600 mg in weight. When the therapeutic agent is an anesthetic agent, the suppository typically comprises from about 1 mg to about 100 mg of anesthetic agent. More typically, the suppository comprises from about 30 mg to about 60 mg of anesthetic agent. Typically, the suppository comprises from about 0.5 mg to about 100 mg of buffering agent; more typically, the suppository comprises from about 1 mg to about 20 mg of buffering agent. Typically, the suppository is in a configuration selected from the group consisting of a cylinder, a cone, and an ellipsoid. In one alternative, the suppository is an elongated structure with a transverse dimension of from about 1 mm to about 10 mm; typically, the transverse dimension is from about 3 mm to about 6 mm. In another alternative, the suppository is an elongated structure with a length of from about 5 mm to about 50 mm; typically, the length is from about 15 mm to about 35 mm. Typically, the suppository comprises a quantity of buffering agent that comprises from about 1 percent to about 30 percent by weight of the overall weight of the suppository.

The suppository can further comprise a quantity of a suspending agent sufficient to prevent active ingredients within the suppository from aggregating. The suspending agent can be silica.

The suppository can further comprise a therapeutically effective quantity of an antibacterial agent or an antifungal agent to treat bacterial or fungal cystitis.

In another alternative, a urethral suppository according to the present invention can comprise a plurality of distinct layers, each layer comprising a carrier base material, a therapeutic agent, and a buffering agent, wherein at least one of the identity of the carrier base material in a layer, the identity of the therapeutic agent in a layer, the identity of the buffering agent in a layer, the quantity of the carrier base material in a layer, the quantity of the therapeutic agent in a layer, the quantity of the buffering agent in a layer, and the shape of a layer varies between at least two of the layers of the suppository. The suppository can comprise two layers, three layers, or four layers; different numbers of layers are also possible. Typically, in this alternative, the therapeutic agent in at least one layer of the urethral suppository is an anesthetic agent. Alternatively, the therapeutic agent in at least two layers of the urethral suppository is an anesthetic agent, and the anesthetic agents in two layers of the urethral suppository are different anesthetic agents. In another alternative, the anesthetic agent in one layer of the urethral suppository is a first anesthetic agent with a rapid onset and the anesthetic agent in another layer of the urethral suppository is a second anesthetic agent with a slower onset than the onset of the anesthetic agent with a rapid onset, but with a longer half-life than the half-life of the anesthetic agent with a rapid onset, the layer including the first anesthetic agent being located closer to the surface of the urethral suppository than the layer including the second anesthetic agent. The first anesthetic agent can be lidocaine, and the second anesthetic agent can be tetracaine.

In still another alternative, the therapeutic agent in one layer of the urethral suppository is an anesthetic agent, and the therapeutic agent in another layer of the urethral suppository is a therapeutic agent other than an anesthetic agent, the layer including the anesthetic agent being located closer to the surface of the urethral suppository than the layer including the therapeutic agent other than an anesthetic agent. Typically, the anesthetic agent is lidocaine. The therapeutic agent other than an anesthetic agent can be selected from the group consisting of an anti-infection agent, an anti-incontinence agent, an anti-inflammatory agent, and an anti-cancer agent.

In still another alternative, the urethral suppository includes therein at least two layers differing in the composition or quantity of the carrier base material in the layers. The two layers can differ in the concentration of an agent that regulates melting time, such as paraffin.

One or more of the layers can include a polysaccharide. If one or more of the layers includes a polysaccharide, and at least one of the identity of the polysaccharide in a layer and the quantity of the polysaccharide in the layer can vary between at least two of the layers of the suppository. At least one of the layers can include a suspending agent. At least one of the layers can include a therapeutically effective quantity of an antibacterial agent or an antifungal agent.

In another possible alternative for multilayer urethral suppositories according to the present invention, at least one of the layers of the suppository is shaped to focus the effect of the suppository in a specific section of the suppository.

Some embodiments of a method for manufacturing a urethral suppository include combining an anesthetic agent and a buffering agent in a liquid carrier base material until the anesthetic agent and the buffering agent have dissolved or been suspended in the liquid carrier base material. The mixture of the liquid carrier base material, the anesthetic agent, and the buffering agent is then formed into a suppository that is configured to be deployed within a patient's urethra. Such embodiments can also include combining a polysaccharide with the liquid carrier base material prior to the formation of the suppository. Typically, the step of forming the mixture into a suppository results in a finished suppository having a weight of from about 10 mg to about 1000 mg. Typically, the quantity of buffering agent combined with the therapeutic agent in the liquid base material is sufficient to produce a pH of from about 7 to about 12 in the finished suppository.

A method for manufacturing a multilayered suppository according to the present invention comprises the steps of:

(1) combining a therapeutic agent and a buffering agent in a liquid carrier base material until the therapeutic agent and the buffering agent have dissolved or been suspended in the liquid carrier base material; and (2) forming the liquid carrier base material, therapeutic agent, and buffering agent mixture into one or more layers of a multi-layered suppository that is configured to be deployed within the urethra of a patient.

A method of treating at least a portion of the urinary tract of a patient using a multilayered suppository according to the present invention comprises the steps of:

(1) providing a multilayered urethral suppository according to the present invention as described above;

(2) deploying the multilayered urethral suppository within the patient's urethra; and (3) allowing the multilayered suppository to disintegrate and release the therapeutic agent and the buffering agent from at least one of the layers of the multilayered suppository to treat at least a portion of the urinary tract of the patient.

In this method, disintegration of the suppository can comprise melting of the carrier base material of at least one layer of the suppository. Alternatively, in this method, disintegration of the suppository can comprise dissolving the carrier base material of at least one layer of the suppository.

Some embodiments of a method of treating at least a portion of a patient's urinary tract comprise the steps of:

(1) providing a urethral suppository according to the present invention as described above;

(2) deploying the urethral suppository within the patient's urethra; and (3) allowing the suppository to at least partially disintegrate and release the therapeutic agent and the buffering agent to treat at least a portion of the urinary tract of the patient.

Disintegration of the suppository can comprise melting of the carrier base material of the suppository. Alternatively, disintegration of the suppository can comprise dissolving the carrier base material of the suppository.

When the therapeutic agent is an anesthetic, as described above, treating at least a portion of the urinary tract of the patient can comprise treatment of interstitial cystitis. Alternatively, treating at least a portion of the urinary tract of the patient can comprise treatment of urethritis. In an other alternative, when the therapeutic agent is an anesthetic, the urethral suppository can be deployed within the urethra of the patient in order to desensitize the urethra prior to insertion of instrumentation into the urethra. In yet another alternative, when the therapeutic agent is an anesthetic, treating at least a portion of the urinary tract of the patient can comprise the prevention or treatment of pain associated with the urethra or bladder. The urethral suppository can further comprise a polysaccharide, as described above, in which case the polysaccharide replaces or repairs the glycosaminoglycan barrier lining the urinary tract of the patient after insertion of the suppository into the urethra of the patient. In another alternative, the step of deploying the urethral suppository within the patient's urethra can further comprise use of a water-based lubricant.

Some embodiments of a depot for luminal drug delivery include a carrier base material, a therapeutic agent, and a buffering agent formed into a solid structure configured for insertion into a body lumen of a patient. Such embodiments can also include a polysaccharide.

The depot can have a substantially uniform composition. The carrier base material can have a melting point such that the depot is substantially melted at body temperature. As described above, the therapeutic agent is typically an anesthetic agent such as lidocaine, although other therapeutic agents can be incorporated into the depot. The carrier base material can be methyl butyl ketone. Alternatively, as described above, the carrier base material can be a water soluble carrier base.

These features of embodiments of the present invention will become more apparent from the following detailed description when taken in conjunction with the accompanying exemplary drawings.

DETAILED DESCRIPTION OF THE INVENTION

Figure 1:
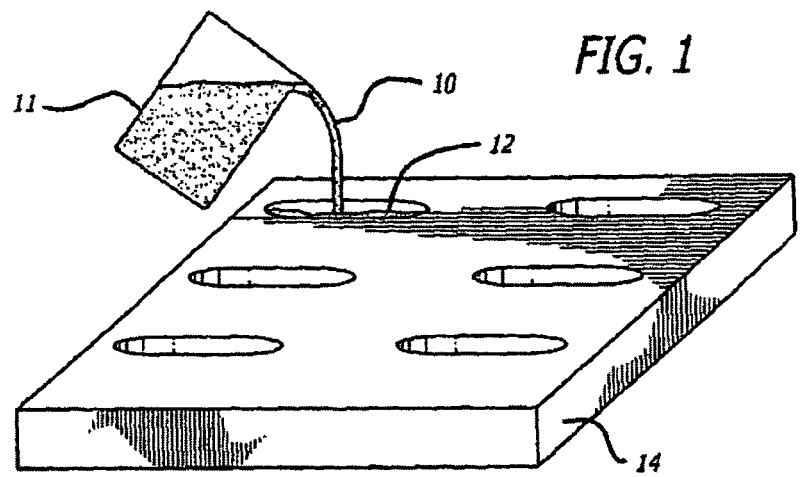
FIG. 1 is a perspective view of an embodiment of a combination of a carrier base material, an anesthetic agent, a buffering agent, and a polysaccharide in liquid form being poured into a suppository mold cavity chamber.

There is currently no definitive diagnostic test for IC, although tests such as the Potassium Sensitivity Test (PST) have been used to identify defects that are fundamental characteristics of IC. The Potassium Sensitivity Test (PST) used a pain, urgency, and frequency questionnaire to identify patients who exhibit a positive reaction to the injection of a concentrated potassium solution into their bladder. The basis for the test is the identification of a fundamental characteristic of IC, which is a breakdown of the glycosaminoglycan (GAG) barrier. Breakdown of the GAG barrier allows components in urine, such as potassium ions, to move into the interstitial spaces. As these components move into the interstitial spaces, they activate sensory nerves that result in pain and begin an inflammatory response. The inflammatory response begins a cascade of events, including the activation of mast cell mediators, further activating sensory nerves resulting in more intense and prolonged pain. The inflammatory response is also considered to play a key role in the breakdown of the GAG layer. An objective in the treatment of IC is to reduce the inflammatory response by inhibiting the activation of sensory nerves. Inhibiting nerve activation reduces the patient's pain and slows or stops the degradation of the GAG barrier. Inhibition of sensory nerves can be achieved using anesthetic drugs, such as lidocaine, procaine, and analogous local anesthetics, which serve to inhibit ionic fluxes required for the initiation and conduction of nerve impulses.

In the urinary tract, the topical delivery of drugs requires overcoming the natural GAG barrier that prevents materials from moving from the luminal space into the interstitium of the urinary tract. Thus, for a topically delivered drug to effectively treat IC, it must pass through the GAG barrier to reach the appropriate urinary tract tissues. At the same time, as it passes through the GAG barrier, the drug must not disable or damage the barrier or negatively affect its function in blocking harmful components in urine. The embodiments disclosed herein include methods for effectively delivering topical drugs to urethral tissue, surrounding tissue, or both, without adversely affecting the GAG barrier of the urinary tract.

Although IC is considered a disease of the bladder, researches have described a urethral component to the disease. This is not surprising as many neural and systemic networks are shared by the bladder and urethra. Unlike the bladder, the urethra is a collapsed tube in its resting stage and open to allow urine to pass out of the bladder. Therefore, any liquid or gel material placed in the urethra would be pushed out of the urethra into the bladder or out of the body. To treat the urethra, a medication can be incorporated into a structure that is retained in the urethra for a period of minutes to hours. Embodiments of a drug delivery system include a suppository base as a means to expose the urethra to medication for periods of time from minutes to hours. The formulation of the delivery system including the type of base materials used as a delivery vehicle, the concentration of drug, and the ratio of drug to buffering agent can be chosen so as to produce an efficient mechanism for delivering the therapeutic agent. Size can be an important aspect for the performance of a urethral suppository and for patient tolerance of the suppository, and thus is a consideration in any suppository formulation. The female urethra is approximately 3-4 cm in length. Most patients, both male and female, can tolerate an object placed in their urethras up to about 19 Fr (6.3 mm) without major discomfort. The maximum size of a urethral suppository that comfortably fits in the female urethra is about 2.5 cm in length and about 0.65 cm in diameter or transverse dimension. One difficulty with the performance of previously available urethral suppositories has been formulating a suppository that fits comfortably in both the male or female urethra yet contains enough drug to produce the desired therapeutic effect while maintaining the functional characteristics of a suppository.

Embodiments include a urethral suppository formulated to prevent or treat symptoms of the urethra and surrounding organs due to urethral procedures or diseases by enhancing the absorption of a drug included in the suppository into body tissues without adversely affecting the natural defense mechanisms of these tissues. This unique formulation is adapted to allow the active therapeutic agent to pass through the GAG barrier that lines the urethra and the urinary tract. Adverse effects on the GAG barrier that might otherwise be caused by the suppository can be mitigated or eliminated by the presence of a suitable polysaccharide included in the suppository formulation.

Embodiments of urethral suppositories include formulations including a therapeutic agent which is included in the suppository mixture. One preferred class of therapeutic agent is an anesthetic agent. A particularly preferred anesthetic agent is lidocaine, a neuronal sodium channel blocking agent. Lidocaine is a white solid substance that has a nitrogen atom that can be protonated. The protonated form of lidocaine is a cation that has a positive charge, while the unprotonated form of lidocaine is neutral and thus uncharged. Typically, lidocaine is provided in its protonated form, in which the positive charge is neutralized by a suitable counterion such as a chloride anion, forming lidocaine hydrochloride. When mixed with water, this form of lidocaine creates a solution that is acidic. For 2-5% lidocaine hydrochloride solutions in sterile water, the pH range is from about 5 to about 6, or slightly acidic. It is known that the ionic, positively charge form of lidocaine is not readily absorbed into tissues of many body cavities and organs. It is well known that ions generally have a difficult time penetrating the hydrophobic lipid bilayers that form a major part of cell membranes. This is due to the high free energy required.

However, buffering ionic lidocaine to a higher pH converts it to a lipid soluble form of the drug because the nitrogen atom loses its proton and becomes neutral. This neutral form of the drug is more readily absorbed into tissues, because it more readily passes through the lipid bilayer of the cell membranes.

In its uncharged form, lidocaine is relatively nonpolar. The free, unprotonated lidocaine molecule is a weak base because of the presence of the amide bond and the secondary amine group. However, the lidocaine molecule will be substantially protonated at a pH lower than the pKa of lidocaine. It will be substantially unprotonated at a pH higher than the pKa of lidocaine; if the pH of the solution is equal to the pKa of lidocaine, which is 7.8, the concentrations of the protonated and unprotonated forms of lidocaine will be equal. This relationship is expressed mathematically by the Henderson-Hasselbalch equation: $[\text{Unprotonated}]/[\text{Protonated}] = 10^{pH-pKa}$.

As described above, lipid molecules are a primary component of cell membranes and are known to be extremely hydrophobic. In the bladder and urethra, the lipid membranes of the urothelial cells are shielded from direct contact with urine by the presence of the GAG barrier. GAG molecules readily attract water molecules creating a hydrated mucous layer that is a primary component of the layer that lines the urethra and the bladder luminal wall. The water molecules in the hydrated mucous layer have a slight negative charge that repels other negatively-charged ionic species. However, uncharged lidocaine molecules are nonpolar and as such are more lipophilic than hydrophilic; such lidocaine molecules can still readily pass through the hydrated mucous layer. Accordingly, they easily and efficiently pass through the mucous layer and cell membranes of the bladder and urethral tissue cells.

Although lidocaine is a preferred anesthetic, compositions and methods according to the present invention are not limited to the use of lidocaine as an anesthetic component. Other anesthetics or combinations thereof can be used, including, but not limited to, lidocaine, benzocaine, bupivacaine, articaine, cocaine, etidocaine, flecamide, mepivacaine, pramoxine, prilocalne, procaine, chloroprocaine, oxyprocaine, proparacaine, ropivacaine, tetracaine, dyclonine, dibucaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Of these, beside lidocaine, preferred anesthetics include prilocalne, benzocaine, mepivacaine, etidocaine, articaine, bupivacaine, procaine, and tetracaine.

Several carrier base materials and buffering agents can be used to create a buffered local anesthetic drug delivery system. Examples of carrier base materials can include, but are not limited to, paraffin, theobroma oil, modified theobroma oil products, gelatins, glycerinated gelatins, polyethylene glycols (PEGs), glycerols, hydrogenated vegetable oils, cocoa butter, methyl butyl ketone (MBK), celluloses, polyvinyl alcohol, polyvinylpyrrolidone, polyacrylamide, polyphosphourethanes, polyoxyl stearate, ethylene oxide polymers, fatty acid bases, and the like. These materials can be used individually or in combination. A particularly preferred carrier base material is methyl butyl ketone. In one alternative, the base material or base materials has a melting point such that the suppository is substantially melted at body temperature. In another alternative, the base material or base materials have a melting point of from about 36° C. to about 38° C. In addition, a carrier base material that is water soluble can also be useful in some alternatives. The melting time of embodiments of the carrier base material or combination of carrier base materials can be adjusted by the addition of paraffin to the liquid mixture to achieve a melting time from about 5 minutes to about 15 minutes.

Examples of buffering agents include, but are not limited to, sodium bicarbonate buffer, calcium bicarbonate buffer, tris(hydroxymethyl)aminomethane (Tris or THAM), MOPS (3-(N-morpholino)propanesulfonic acid) buffer, HEPES (N-(2-hydroxyethyl)piperazine-N'-(2-ethanesulfonic acid) buffer, ACES (2-[(2-amino-2-oxoethyl)amino]ethanesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS(N-(2-hydroxyethylpiperazine)-N'-(3-propanesulfonic acid), buffer, HEPPSO (N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropanesulfonic acid) buffer; TAPS (N-tris [hydroxymethyl)methyl-3-aminopropanesulfonic acid) buffer, TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, 2-amino-2-methyl-1-propanol buffer, or another buffer that can buffer the composition to be administered at the appropriate pH value, as well as combinations of these buffers. The buffer to be selected, and the concentration of the buffer to be used, can be chosen by one of ordinary skill in the art to buffer the composition to be administered at a pH value that is close to the isoelectric point of the local anesthetic. For lidocaine, this pH value is 7.9. For bupivacaine, it is 8.1. For etidocaine, it is 7.7. Typically, the pH achieved by the use of the buffer is between about 7.0 and about 12.0. More typically, the pH achieved by the use of the buffer is between about 7.0 and about 9.5. Typically, when bicarbonate buffer is used, it is sodium bicarbonate buffer; however, other counterions can be used as described above.

The carrier base material can further include additional components such as preservatives. Suitable preservatives include, but are not limited to methylparaben, ethylparaben, propylparaben, butylparaben, chlorphenesin, chlorobutanol, sorbic acid, thimerosal, and other preservatives commonly used in the art for pharmaceutical compositions, including suppositories. Typically, the preservative is methylparaben or propylparaben.

The carrier base material can further include an alkali as a pH adjusting agent to adjust the pH to an appropriate value. The alkali can be, but is not limited to, sodium carbonate, sodium hydroxide, potassium hydroxide, magnesium oxide, or another alkali. However, in many applications, particularly those in which the suppository is to be administered as part of treatment of interstitial cystitis, it is preferred to use alkalis in which the cation is other than potassium. This is because of the role that abnormal permeability of the urothelium to potassium plays in the etiology of interstitial cystitis, so administration of potassium salts is preferably avoided. The alkali is to be distinguished from the buffering agent.

One useful combination of carrier base material and buffering agent is MBK and sodium bicarbonate. The melting point of MBK can be adjusted to alter its disintegration rate via a melting process over a wide range of time at body temperature. Adjustment of the melting point of MBK can be carried out by adding selected amounts of paraffin. MBK also has the ability to dissolve lidocaine. Sodium bicarbonate can be useful as a buffering agent for some embodiments of urethral suppositories because it has the ability to buffer the pH value in the range of 8-9 in combination with lidocaine and the carrier base. Examples of suitable formulations are provided in the Examples below.

Silica can also be added as a suspending agent to prevent the active ingredients within the suppository from aggregating. The use of silica or other suspending agent results in a suppository that has a substantially uniform composition.

Urethral suppositories according to the present invention can be formed by mixing or combining components into a mixture and forming the mixture into a solid suppository. For example, such methods can include combining a therapeutic agent in the form of an anesthetic agent and a buffering agent in a liquid carrier base material. As described in greater detail below, a polysaccharide can also be combined with the liquid carrier base material before formation of the suppository. The combined components can be stirred, heated, or both until the anesthetic agent and the buffering agent have been dissolved or suspended in the liquid carrier base material. For example, the carrier base material can be warmed in a both having a temperature of from about 35° C. to about 45° C. Once the carrier base material is warmed, a suitable anesthetic agent, such as lidocaine, can be added. After the anesthetic agent has dissolved or has been otherwise suspended in solution, the mixture can continue to be heated or have the temperature raised to a temperature of from about 60° C. to about 80° C. Thereafter, the mixture can be titrated with a buffering agent, such as sodium bicarbonate, to a pH of from about 7.5 to about 9 while gently stirring the mixture. In some embodiments, the mixture may lose its grainy appearance and become clear as all components are all dissolved in the carrier base material. Once the components have been suitably mixed, the liquid carrier base material, anesthetic agent, and buffering agent mixture can be formed into a suppository or other type of solid depot that is configured to be deployed within a patient's urethra or other body lumen.

FIG. 1 shows a perspective view of an embodiment of a combination of a carrier base material, an anesthetic agent, a buffering agent, and, optionally, a polysaccharide in a mixture 10 in liquid form being poured from a container 11 into a suppository mold cavity 12. A mold body 14 includes six individual mold cavities 12; each individual mold cavity 12 has an elongated configuration with rounded or spherically shaped ends. Once one or more of the mold cavities 12 have been filed with the combined mixture 10, the combined mixture 10 is allowed to harden and to form a solid structure. In some cases, the mold body 14 can be refrigerated overnight, after which the mixture 10 that has hardened into suppositories in the mold cavities 12 is removed from the mold; the resulting suppositories can be individually packaged for distribution or storage. The suppositories can also be stored at lowered temperatures, such as from about 0° C. to about 10° C. prior to use.

Figure 2:
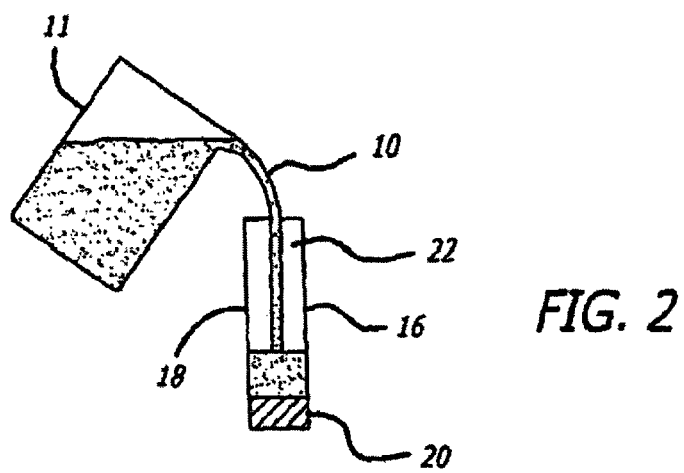
FIG. 2 is a diagrammatic view of an embodiment of a combination of a carrier base material, an anesthetic agent, a buffering agent, and a polysaccharide in liquid form being poured into a suppository mold cavity embodiment showing the layers formed within the mold cavity chamber.

FIG. 2 is a perspective view of mixture 10 being poured from container 11 into a cylindrical suppository mold 16. The suppository mold 16 has a barrel shaped body portion 18 having a substantially round cross section with a removable plug 20 disposed at the bottom of a mold cavity chamber 22. After the mold cavity chamber 22 has been filled to a desired level, the combined mixture 10 containing the carrier base material, anesthetic agent, buffering agent, and, optionally, polysaccharide is allowed to harden. Thereafter, the plug 20 can be removed and the newly formed suppository pushed from the mold cavity chamber 22. The plug 20 can also be used to push the newly formed suppository from the mold cavity chamber 22.

Figure 3:
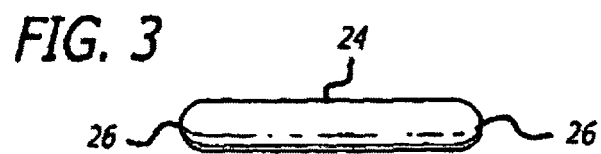
FIG. 3 is a perspective view of a urethral suppository embodiment.

FIG. 3 is a perspective view of a urethral suppository embodiment 24. The suppository 24 has an elongated cylindrical configuration with rounded or spherically shaped ends 26; however, other configurations such as conical or ellipsoidal can alternatively be used. As discussed above, the size of the suppository 24 is a significant parameter in some applications. In particular, for urethral suppositories 24, it can be useful to have as large a suppository as possible while maintaining an acceptable level of patient discomfort. Some embodiments of a urethral suppository 24 can have a length of about 5 mm to about 50 mm; typically, the length is from about 15 mm to about 35 mm. Such embodiments can have a transverse dimension of from about 1 mm to about 10 mm; typically, the transverse dimension is from about 3 mm to about 6 mm. The overall weight of some embodiments of the suppository 24 can be from about 10 mg to about 1000 mg; more typically, the overall weight is from about 50 mg to about 750 mg; preferably, the overall weight is from about 400 mg to about 600 mg. The overall weight can be chosen depending on the appropriate size and shape of the suppository 24.

The carrier base material for the suppository can include a variety of suitable materials, as described above, including but not limited to paraffin, theobroma oil, modified theobroma oil products, gelatins, glycerinated gelatins, polyethylene glycols (PEGs), glycerols, hydrogenated vegetable oils, cocoa butter, methyl butyl ketone (MBK), celluloses, polyvinyl alcohol, polyvinylpyrrolidone, polyacrylamide, polyphosphourethanes, polyoxyl stearate, ethylene oxide polymers, fatty acid bases, and the like. These materials can be used individually or in combination.

Suitable anesthetic agents for the suppository 24 can include lidocaine, benzocaine, bupivacaine, articaine, cocaine, etidocaine, flecamide, mepivacaine, pramoxine, prilocalne, procaine, chloroprocaine, oxyprocaine, paraproaine, ropivacaine, tetracaine, dyclonine, dibucaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof, as well as combinations thereof. Preferred anesthetic agents include lidocaine, prilocalne, benzocaine, mepivacaine, etidocaine, articaine, bupivacaine, procaine, and tetracaine. A particularly preferred anesthetic agent is lidocaine. The anesthetic effect of all of these anesthetic agents will increase when mixed with suitable buffers. However, by mixing buffering agents at different concentrations with these anesthetic agents, different anesthetic effects over varying periods of time can be achieved. It can be useful for some embodiments to have a therapeutic agent that is configured to inhibit the conduction or initiation of nerve impulses. Typically, the quantity of anesthetic agent incorporated in a suppository 24 according to the present invention is sufficient to prevent or ameliorate a urinary tract disorder. Typically, the urinary tract disorder is interstitial cystitis. Alternatively, the urinary tract disorder is urethritis. Some embodiments of the urethral suppository 24 can include about 1 mg to about 100 mg of anesthetic agent; typically, the urethral suppository 24 includes from about 10 mg to about 75 mg of anesthetic agent; more typically, the urethral suppository 24 includes about 30 mg to about 60 mg of anesthetic agent. The quantity of anesthetic agent included in the urethral suppository 24 can be chosen according to the size and shape of the urethral suppository 24 and the disease or condition that the urethral suppository 24 is to treat.

Buffering agents that can be used for embodiments of the suppository 24 can include buffering agents that are present in a quantity such that the buffering agent or agents buffers the suppository at a pH that ensures that a sufficient portion of an anesthetic agent that is present in the suppository is present in an uncharged state so that the anesthetic agent can cross cell membranes of cells surrounding the urethra. Typically, the buffering agent can maintain a pH of the urethral suppository 24 in a range of from about 7 to about 12. More typically, the buffering agent can maintain a pH of the urethral suppository 24 in a range of from about 7 to about 9. As described above, suitable buffering agents include, but are not limited to, sodium bicarbonate buffer, calcium bicarbonate buffer, tris (hydroxymethyl)aminomethane (Tris or THAM), MOPS (3-(N-morpholino)propanesulfonic acid) buffer, HEPES (N-(2-hydroxyethyl)piperazine-N'-(2-ethanesulfonic acid) buffer, ACES (2-[(2-amino-2-oxoethyl)amino]ethanesulfonic acid) buffer, ADA (N-(2-acetamido)-2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2- aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS(N-(2-hydroxyethylpiperazine)-N'-(3-propanesulfonic acid), buffer, HEPPSO (N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropanesulfonic acid) buffer; TAPS (N-tris[hydroxymethyl]methyl-3-aminopropanesulfonic acid) buffer, TAPSO (3[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, 2-amino-2-methyl-1-propanol buffer, or another buffer that can buffer the composition to be administered at the appropriate pH value, as well as combinations thereof. Preferred buffering agents include sodium bicarbonate and tris(hydroxymethyl)aminomethane (Tris or THAM) buffer. A particularly preferred buffering agent is sodium bicarbonate. Combinations of different buffering agents and anesthetic agents will have different stability properties, affecting their efficacy when stored for long periods of time. The choice of buffering agent can also be affected by the ability of the buffering agent to maintain a uniform distribution of the anesthetic agent throughout the suppository 24. One of ordinary skill in the art can make these determinations depending on parameters such as the stability of buffering agents and anesthetic agents, and physical and chemical properties of buffering agents and anesthetic agents including, but not limited to, molecular weight, molecular conformation, polarity, and relative hydrophobicity or hydrophilicity. Some embodiments of the urethral suppository 24 can include from about 0.5 mg to about 100 mg of buffering agent. Typically, the urethral suppository included from about 0.75 mg to about 50 mg of buffering agent; more typically, the urethral suppository 24 includes from about 1 mg to about 20 mg of buffering agent. The quantity of the buffering agent in the urethral suppository 24 can be chosen according to the size and shape of the urethral suppository 24 and the disease or condition that the urethral suppository 24 is to treat. Some embodiments of the urethral suppository 24 can contain a quantity of buffering agent that comprises from about 1 percent to about 30 percent by weight of the overall weight of the urethral suppository 24. Typically, the urethral suppository 24 contains a quantity of buffering agent that comprises from about 2.5 percent to about 20 percent of the overall weight of the urethral suppository 24. More typically, the urethral suppository 24 contains a quantity of buffering agent that comprises from about 5 percent to about 10 percent by weight of the overall weight of the suppository 24. The urethral suppository 24 typically contains at least one buffering agent selected from the buffers listed above. Alternatively, the urethral suppository 24 can contain a combination of buffering agents such that the combination of buffering agents is compatible with the anesthetic agent or combination of anesthetic agents and such that each buffering agent in the combination is compatible with the other buffering agents in the combination and with other ingredients in the suppository.

The composition of some embodiments, and particularly some of the buffering agents and/or anesthetic agents, can include pharmaceutically acceptable salts. Pharmaceutically acceptable salts include, but are not limited to, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts can be found in, for example, Remington, *The Science and Practice of Pharmacy* ($20^{th}$ ed, Lippincott, Williams & Wilkins (2000)), which is incorporated herein in its entirety by reference.

Embodiments of the urethral suppository 24 can further include a polysaccharide material, such as a mucopolysaccharide, configured to replace or repair the GAG layer or barrier of at least a portion of a patient's urinary tract, such as the urethra. Typically, the polysaccharide is an anionic polysaccharide. If present, the polysaccharide is typically present in the urethral suppository 24 in a sufficient quantity to prevent or ameliorate a urinary tract disorder. Typically, the urinary tract disorder is interstitial cystitis. Alternatively, the urinary tract disorder is urethritis.

The anionic polysaccharide is typically a glycosaminoglycan. Glycosaminoglycans are abundant naturally occurring polysaccharides that have a net negative charge due to carboxylic acid or sulfate groups or both. Although Applicants are not bound by this theory, these polysaccharides are believed to have protective effects on the epithelium and to counteract the abnormal permeability of the epithelium to potassium that is characteristic of IC. Preferred anionic polysaccharides include, but are not limited to, hyaluronic acid, hyaluronan, chondroitin sulfate, pentosan polysulfate, dermatan sulfates, heparin, heparan sulfates, keratan sulfates, dextran sulfates, and carrageenan.

Heparin exists in a variety of forms characterized by different degrees of sulfation. Typically, heparin has a molecular weight of from about 2 kDa to about 40 kDa. Heparin and heparan sulfate are both characterized by repeating units of disaccharides containing a uronic acid (glucuronic acid or iduronic acid) and glucosamine, which is either N-sulfated or N-acetylated. The sugar residues can be further O-sulfated at the C-6 and C-3 positions and the C-2 position of the uronic acid. There are at least 32 potential unique disaccharide units in this class of compounds. Five examples of sugars occurring in heparin are: (1) $\alpha$-L-iduronic acid 2-sulfate; (2) 2-deoxy-2-sulfamino-$\alpha$-D-glucose 6-sulfate; (3) $\beta$-D-glucuronic acid, (4) 2-acetamido-2-deoxy-$\alpha$-D-glucose, and (5) $\alpha$-L-iduronic acid. Heparin is measured by its specific anticoagulation activity in units. As used herein, the term "units" refers to specific activity in International Units (IU) and/or United States Pharmacopoeia (USP) units. As used herein, the term "USP unit" refers to the quantity of heparin that prevents 1.0 ml of citrated sheep plasma from clotting for 1 hour after the addition of 0.2 ml of 1% $CaCl_2$ at 20° C. when compared to a USP reference standard (defined as units/ml). As used herein, the term "International Unit" or "IU" refers to the quantity of heparin that is active in assays as established by the Fifth International standard for Unfractionated Heparin (WHO-5) (defined as International Units/ml) (Linhardt, R. J. & Gunay, N. S. (1999) Semin Thromb Hemost 25, 5-16). In some embodiments, heparin is a higher molecular weight species ranging from 8,000 to 40,000 daltons. As used herein, "low-molecular-weight heparins" refers to a lower molecular weight (LMW) species ranging from 2,000 to 8,000 daltons. Also included as glycosaminoglycans within the scope of the invention are pentosan polysulfate sodium of molecular weight ranging from 4,000 to 6,000 daltons, dalteparin, enoxaparin and the like. LMW heparins are made by enzymatic or chemical controlled hydrolysis of unfractionated heparin and have very similar chemical structure to unfractionated heparin except for some changes that may have been introduced due to the enzymatic or chemical treatment. While not intending to limit the mechanism of action of the invention's compositions, it is the inventors' view that mechanism of action of these drugs is similar to that of full-length heparin. LMW heparins are usually isolated from bulk heparin. Because of the negative charge of these polysaccharides due to the occurrence of sulfate groups and/or carboxylic acid groups in them, they are administered in the form of salts, with an appropriate cation to neutralize the negative charges on the acid groups. Typically, the cation is sodium. However, other physiologically tolerable counterions that do not induce urinary tract dysfunctions such as magnesium and aluminum, as well as salts made from physiologically acceptable organic bases such as, but not limited to, trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, dibenzylpiperidine, N-benzyl-β-phenethylamine, dehydroabietylamine, N,N'-bisdehydroabietylamine, glucamine, N-methylglucamine, collidine, quinine, quinoline, and basic amino acids such as lysine and arginine, can be used. These cationic counterions can alternatively be used as the counterions with anionic buffers such as bicarbonate, as well. These salts may be prepared by methods known to those skilled in the art. However, it is generally undesirable to use potassium as a counterion due to its role in the etiology of the conditions and syndromes being treated. Other glycosaminoglycans can be used in suppositories and methods according to the invention, including low molecular weight (LMW) glycosaminoglycans, naturally derived glycosaminoglycans, biotechnologically prepared glycosaminoglycans, chemically modified glycosaminoglycans, and synthetic glycosaminoglycans.

Typically, when urethral suppositories 24 according to the present invention contain polysaccharide, the quantity of polysaccharide is from about 0.5 mg to about 100 mg of polysaccharide. More typically, the quantity of polysaccharide is from about 0.75 mg to about 50 mg of polysaccharide. Preferably, the quantity of polysaccharide is from about 1 mg to about 20 mg of polysaccharide. The quantity of polysaccharide in a urethral suppository 24 according to the present invention can be chosen according to the size and shape of the urethral suppository 24 and the disease or condition that the urethral suppository 24 is to treat, as well as the molecular weight of the polysaccharide and the specific activity of the polysaccharide.

Silica can also be added as a suspending agent to prevent the active ingredients within the urethral suppository 24 from aggregating. Silica can comprise from about 0.1 percent to about 5 percent by weight of a urethral suppository 24 according to the present invention. Typically, silica comprises from about 0.5 percent to about 2.5 percent by weight of a urethral suppository 24 according to the present invention. Other suspending agents can alternatively be used and are well-known to those skilled in the art.

Figure 4:
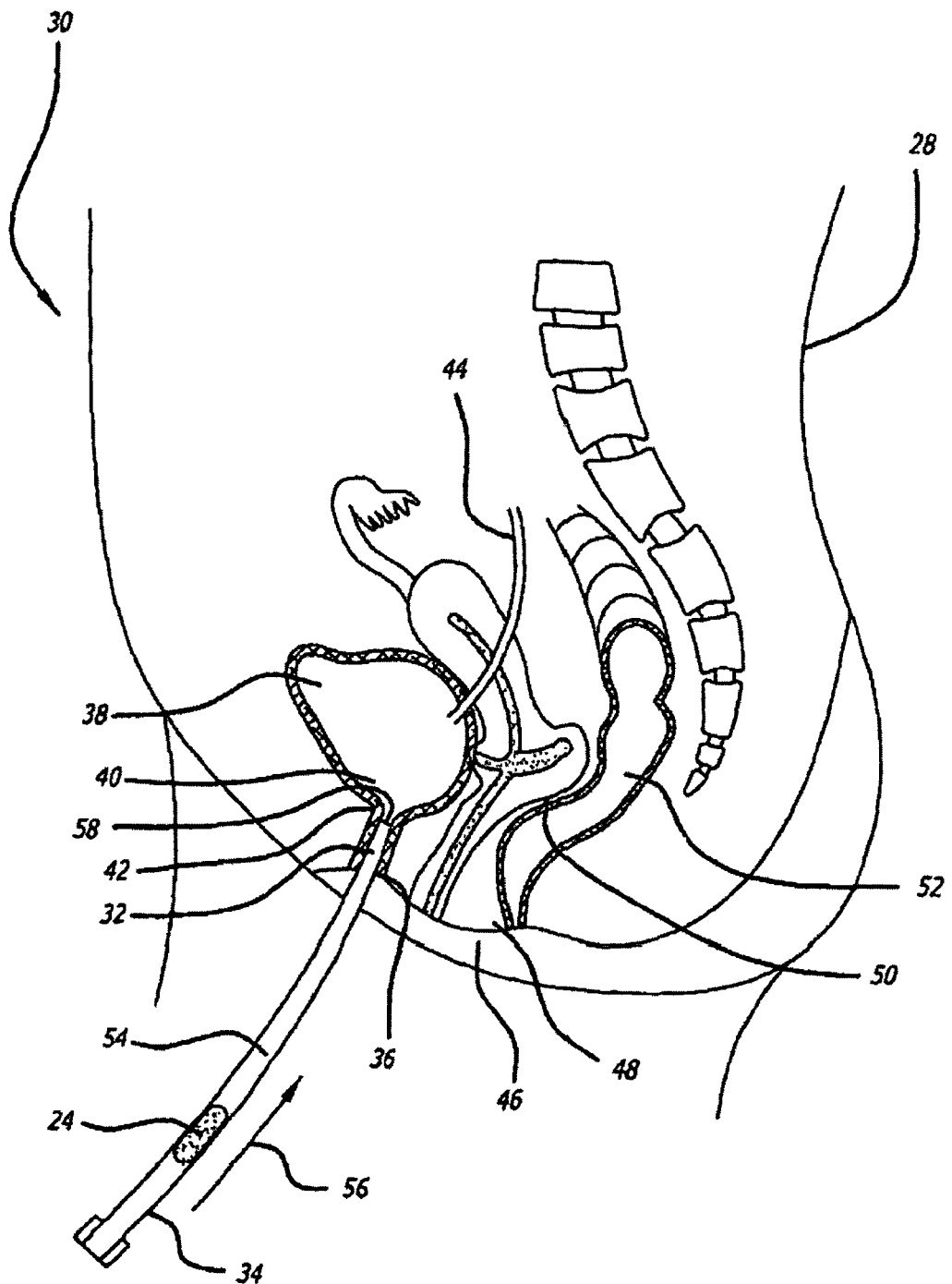
FIG. 4 is a side view in partial section of a distal portion of a delivery catheter disposed within a urethra of a patient and a urethral suppository being advanced distally within the delivery catheter.

Once the urethral suppository 24 has been formed or otherwise manufactured, it can be deployed within the body 28 of a patient 30 in order to treat a variety of conditions, including IC, urethritis, pain from a number of conditions, or employed for pre-procedure sensitization or other uses. Although a human patient is depicted in FIG. 4 and the embodiments disclosed herein would be typically used for human patients, they can also be used in veterinary medicine to treat similar or identical indications in animals. For example, they could be used to treat a socially or economically important animal such as a horse, a cow, a sheep, a goat, a donkey, a mule, a dog, a cat, a pig, or another socially or economically important animal. FIG. 4 is a side view in partial section of a distal portion 32 of a delivery catheter 34 disposed within a urethra 36 of a patient. FIG. 4 illustrates the patient's urinary tract including the bladder 38, bladder neck 40, urethra 42, and ureter 44. Also shown are some of the issues surrounding the female patient's urinary tract including the labia minora 46, urethral os 48, vagina 50, and rectum 52. The urethral suppository 24 is shown being advanced distally within an inner lumen 54 of the delivery catheter 34 towards the urethra 36 of the patient 30, as indicated by arrow 56. The delivery catheter 34 is an elongated tubular member having a length of about 10 cm to about 100 cm, an outer transverse dimension or diameter of about 19 Fr. and an inner lumen having an inner transverse dimension or diameter of up to about 10 mm. The delivery catheter 34 can have any suitable construction, including that of an extruded polymer tube that can optionally be reinforced with braided material or the like. Materials such as polyethylene, polyurethane, nylon, or the like can be used. Once the suppository has been advanced to the distal portion 32 of the delivery catheter 34 and ejected from a distal end 58 of the delivery catheter 34, the delivery catheter 34 can be withdrawn from the urethra 36 of the patient 30.

Figure 5:
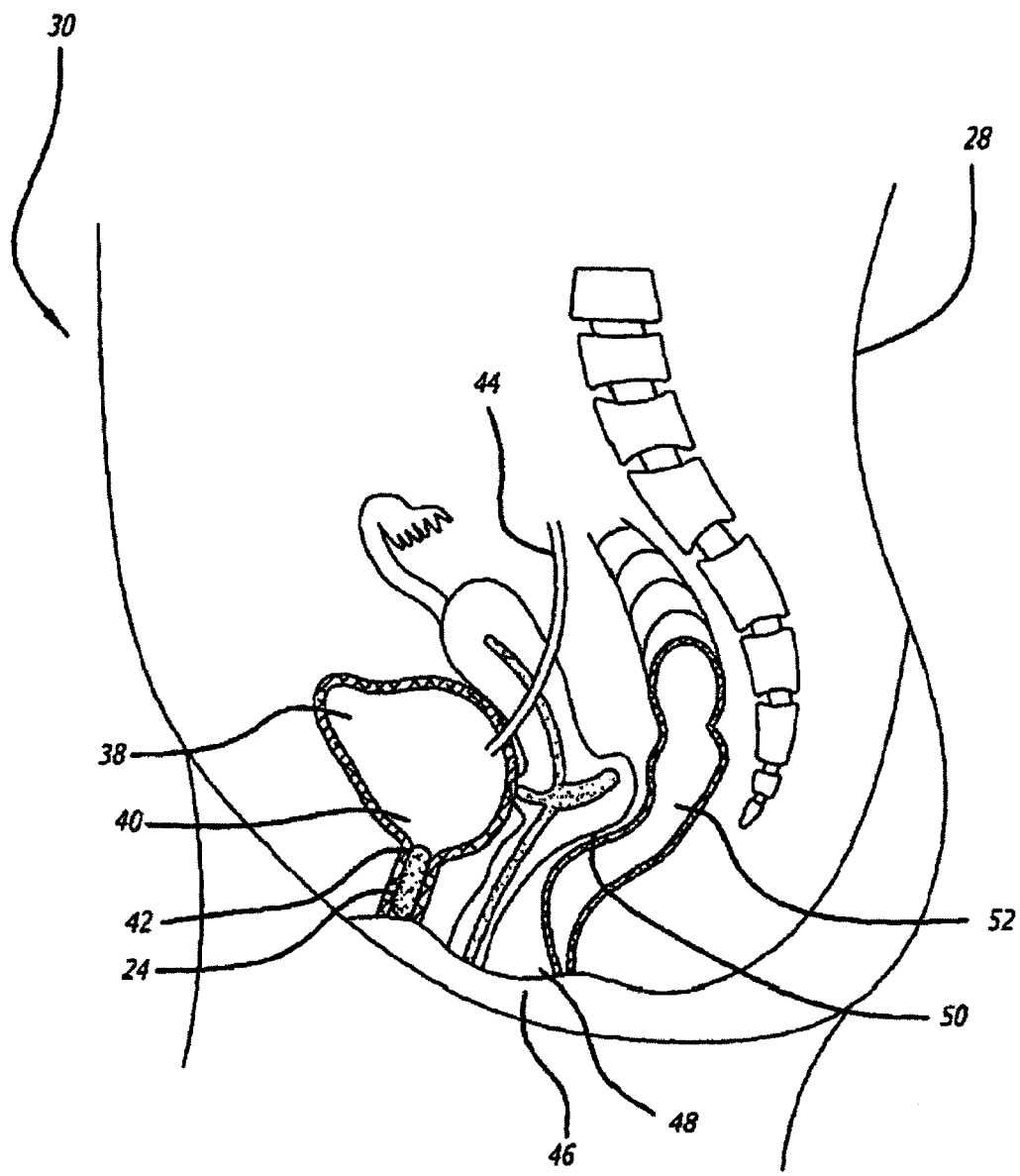
FIG. 5 is a side view in partial section of the urethral suppository disposed within the urinary tract of the patient with the delivery catheter withdrawn.

FIG. 5 shows the patient 30 of FIG. 4 with the suppository 24 disposed within the urethra, the delivery catheter 34 having been withdrawn. Once the suppository 24 has been deployed within the urethra 36 or other body lumen, the carrier base material begins to disintegrate and thereby deliver the buffered anesthetic agent or other therapeutic agent to tissues of the patient's urinary tract and surrounding tissue. The disintegration of the suppository can be carried out by dissolving of the carrier base material for some embodiments, particularly for embodiments having a water-soluble carrier base material. The disintegration of the suppository 24 can also occur due to melting of the carrier base material as a result of exposure to body temperature within the urethra. In either modality, disintegration of the carrier base material exposes the therapeutic agent or agents integrated into the suppository structure 24.

The exact dosage delivered to patient 30 can depend on the subject to be treated, the age of the subject to be treated, the body weight of the subject to be treated, the nature of the disease or condition for which the suppository is administered, such as, but not limited to, interstitial cystitis or urethritis, the severity and course of the disease or condition of the subject to whom the suppository is administered, the response of the subject, and pharmacokinetic considerations such as liver and kidney function that affect the metabolism of any administered therapeutic agent. The optimal concentration and dosage of the therapeutic agent, such as an anesthetic agent, to be delivered can also depend on the specific therapeutic agent such as anesthetic used, the buffering agent used, the carrier base material used, and any optional polysaccharide used. These factors can be determined by those of skill in the medical and pharmaceutical arts in view of the disclosure of the present application. Generally, a therapeutically effective dose is desired. A therapeutically effective dose refers to that amount of the anesthetic agent or other therapeutic agent that results in a degree of amelioration of symptoms prior to treatment. As used herein, the term "treat" or equivalent terminology, including, but not limited to, terminology such as "ameliorate," refers to any detectable improvement, whether subjective or objective, in the urinary tract disorder of the subject to whom the composition is administered. For example, the term "ameliorate" can refer to an improvement as determined by the PORIS scale, PUF scale, or any component of those scales; reduction of pain; reduction of urinary frequency; reduction of urinary urgency; reduction of requirement for narcotic administration; reduction of incontinence; reduction of abnormal permeability of the urothelium to potassium; or improvement in more than one of these parameters. The term "ameliorate" does not state or imply a cure for the underlying lower urinary tract condition. Alternatively, a dosage that prevents a symptom or condition of the urinary tract can be administered. The dosage forms containing effective amounts are within the bounds of routine experimentation, and therefore, are well within the scope of the embodiments disclosed herein. In general, however, a suitable dose of a buffered anesthetic for topical delivery can be in the range of from about 0.1 to about 10 mg/kg of body weight per day, typically in the range of from about 0.2 to about 5 mg/kg of body weight per day, more typically in the range of from about preferably in the range of from about 0.4 to about 2 mg/kg of body weight per day.

A urethral suppository 24 according to the present invention can comprise additional ingredients. For example, the suppository 24 can further comprise a therapeutically effective quantity of an antibacterial agent or an antifungal agent to treat bacterial or fungal cystitis. Suitable antibacterial agents include, but are not limited to: (1) sulfonamides such as sulfanilamide, sulfadiazine, sulfamethoxazole, sulfisoxazole, sulfamethizole, sulfadoxine, and sulfacetamide; (2) penicillins such as methicillin, nafcillin, oxacillin, cloxacillin, dicloxacillin, ampicillin, amoxicillin, bacampicillin, carbenicillin, ticarcillin, mezlocillin, and piperacillin; (3) a combination of trimethoprim plus sulfamethoxazole; (4) quinolones such as nalidixic acid, cinoxacin, norfloxacin, ciprofloxacin, orfloxacin, sparfloxacin, lomefloxacin, fleroxacin, pefloxacin, and amifloxacin; (5) methenamine; (6) nitrofurantoin; (7) cephalosporins such as cephalothin, cephazolin, cephalexin, cefadroxil, cefamandole, cefoxatin, cefaclor, cefuroxime, loracarbef, cefonicid, cefotetan, ceforanide, cefotaxime, cefpodoxime proxetil, ceftizoxime, ceftriaxone, cefoperazone, ceftazidime, and cefepime; (8) carbapenems such as imipenem, meropenem, and aztreonam; (9) aminoglycosides such as netilmycin and gentamicin; (10) tetracyclines such as tetracycline, oxytetracycline, demeclocycline, minocycline, doxycycline, and chlortetracycline; and (11) macrolides such as erythromycin, clarithromycin, and azithromycin. Antifungal agents include amphotericin B, itraconazole, ketoconazole, fluconazole, miconazole, and flucytosine. Other suitable antibacterial agents and antifungal agents are known in the art.

Additionally, still other ingredients can be included in a urethral suppository 24 according to the present invention. Such ingredients can include, for example, a coloring agent, an antioxidant, a chelating agent, and other ingredients typically used in pharmaceutical formulations, including in suppositories. The use of preservatives is described above.

Urethral suppositories according to the present invention can also be constructed with multiple layers. A urethral suppository according to the present invention can be constructed with two, three, or four layers, or more layers, with each layer having a different composition. Several alternatives are possible for the multiple layers. For example, the layers can include the same anesthetic agent, buffering agent, and, if present, polysaccharide, but such that the concentrations of one or more of these components vary from layer to layer. For example, the layers can have the same concentration of buffering agent and polysaccharide, but different concentrations of anesthetic agent. As another alternative, the layers can have different concentrations of anesthetic agent and polysaccharide, but the same concentration of buffering agent. As still another alternative, the layers can have different concentrations of buffering agent, anesthetic agent, and polysaccharide. If silica or another suspending agent is present, its concentration can be varied between layers, or it can be omitted in one or more of the layers. Similarly, if antibacterial or antifungal agents are present, their concentration can be varied between layers or they can be omitted in one or more layers. In another alternative, the layers can include different anesthetic agents, buffering agents, or polysaccharides if present. In this alternative, each of the layers can include a different anesthetic agent, buffering agent, or polysaccharide. Alternatively, several of the layers could include the same anesthetic agent, buffering agent, or polysaccharide, but one or more additional layers could have a different anesthetic agent, buffering agent, or polysaccharide. The same arrangements can apply to additional ingredients such as suspending agents, antibacterial agents, or antifungal agents; they can be varied between layers.

The construction of suppositories including multiple layers with different compositions can be performed in a number of ways known to those in the art. For example, but not by way of limitation, the layers can be assembled sequentially from the inside out, so that a first layer is constructed and then a second layer is constructed on top of the first layer, so that a cross-section would show the first layer inside the second layer and closer to the center of the suppository. Other means of construction of suppositories including multiple layers with different compositions are known in the art.

In general, therefore, a urethral suppository according to this embodiment comprises a plurality of distinct layers, each layer comprising a carrier base material, a therapeutic agent, and a buffering agent, wherein at least one of the identity of the carrier base material in a layer, the identity of the therapeutic agent in a layer, the identity of the buffering agent in a layer, the quantity of the carrier base material in a layer, the quantity of the therapeutic agent in a layer, the quantity of the buffering agent in a layer, and the shape of a layer varies between at least two of the layers of the suppository.

In one alternative, the therapeutic agent in at least one layer of the urethral suppository is an anesthetic agent, as described above. The therapeutic agent in all layers of the urethral suppository can be an anesthetic agent. One or more of the layers can include a polysaccharide, as described above. Where more than one layer includes a polysaccharide, and at least one of the identity of the polysaccharide in a layer and the quantity of the polysaccharide in the layer can vary between at least two of the layers of the suppository. One or more of the layers can include a suspending agent, as described above. One or more of the layers can include a therapeutically effective quantity of an antibacterial agent or an antifungal agent as described above.

In another alternative, the layers can include distinct classes of drugs to treat different disease states or provide different drug profiles, or possess different formulations that would affect the physical properties of the suppository.

Multiple layers of suppository containing different classes of drugs may be used to treat different diseases, which include, but are not limited to infection, incontinence, inflammation or cancer. Suitable anti-infection agents, including but not limited to antibacterial agents, antifungal agents, antiprotozoal agents, and antiviral agents, are known in the art. Similarly, suitable anti-incontinence agents, including but not limited to anticholinergic agents such as propantheline bromide and oxybutynin chloride, are known in the art. Anti-inflammatory agents, including, but not limited to, steroids and non-steroidal anti-inflammatory drugs (NSAIDs), are known in the art. Anti-cancer agents, including, but not limited to, alkylating agents, antimetabolites, Vinca alkaloids, taxanes, epipodophyllotoxins, camptothecins, antibiotics, enzymes, biological response modifiers, platinum coordination complexes, anthracenediones, substituted ureas, methylhydrazine derivatives, adrenocortical suppressants, tyrosine kinase inhibitors, adrenocorticosteroids, progestins, estrogens, antiestrogens, androgens, antiandrogens, gonadotropin-releasing hormone analogues, and monoclonal antibodies, are known in the art. In one example, an anti-cancer agent may be incorporated in the inner layer of a suppository, while the outer layer of suppository contained an anesthetic agent such as lidocaine as described above. In this manner, cancer agents that caused discomfort or pain to the patient could be used because of the anesthetic effect of the anesthetic agent in the outer layer of the suppository. In another example, the outer layer can include a first anesthetic agent with a rapid onset, but short half-life, such as lidocaine, while the inner layer includes a second anesthetic agent with a slower onset, but much longer half-life, such as tetracaine. In this manner, the anesthetic effect to the urethra could be made to occur quickly and last many hours longer than with a suppository containing a single anesthetic agent.

Multiple layers of suppository may also be fabricated to incorporate different formulations to affect the physical properties of the layer, such as melting or dissolution time. Typically, these different formulations alter the composition or quantity of the carrier base material. In one example, the outer layer of a multi-layer suppository can comprise a formulation with a reduced concentration of the agent used to regulate melting time, such as paraffin, while the inner layer contained a higher concentration of the same agent to increase melting time. The outer layer would melt quickly, exposing the urethra to a loading dose of anesthetic agent, while the inner layer would melt slower, providing the urethra a maintenance dose of the same anesthetic agent. In this manner, the anesthetic and therapeutic effect of the suppository would provide an immediate effect that was extended beyond what was achievable by a single layer suppository.

Although the examples presented above describe two layer suppositories, it should be recognized that suppositories including three or more layers are possible and are limited only by the desired final size and the methods used to fabricate the suppository; these multiple layer suppositories can include various arrangements of the layers. Fabrication methods can include, but are not limited to, insert molding or dipping processes. The insert molding process would use one or more inserts that would be placed inside a mold cavity. The outer layer of the suppository would be formed first by pouring the melted suppository material into a mold cavity with an insert that would be removed after the material had cooled and hardened leaving a hollow space within the suppository. A second material can then be poured into the hollow space to form the inner layer of the suppository. Alternatively, a second smaller insert could be inserted to form a third hollow space within the second material for a third material. This same process could be followed as often as practical to create a multilayered suppository.

Insert molding produces suppositories with layers that contain very accurately measured amounts of drugs and ingredients. However, the insert molding process involves many steps, thus making it expensive and complex. A less expensive, but less accurate method for fabricating multilayered suppositories is using a dipping process. The first step is to form the innermost layer is using conventional suppository fabrication methods. The formed suppository is then dipped in a second material. Changing parameters of the dipping process can regulate the thickness of the second layer of material. These parameters include, but are not limited to, the viscosity of the second material, the speed of withdrawal of the suppository from the second material and the temperature of each component in the system. This process can be repeated to create multilayered suppositories.

Finally, it should be recognized that the multilayered suppository can be fabricated such that the geometry of the individual layers are different from the geometry of the total suppository or from one another. A layer of suppository material may be thickened or thinned or shaped to focus its effect in a specific section of the suppository. The advantages of such a multilayered suppository structure are to provide more or less drug to specific areas of the urethra, such as the prostate, a urethral sphincter, or the bladder neck. The complexity of the different geometries is limited in some part by the fabrication process, with insert molding techniques providing more flexibility than dipping processes in creating more complicated and precise geometries.

Figure 17:
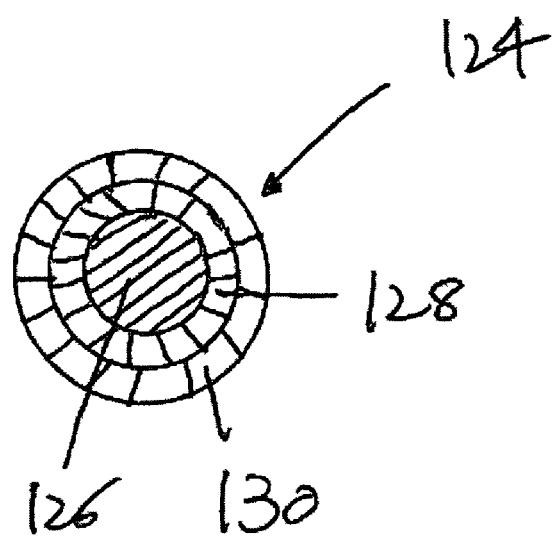
FIG. 17 is a cross-section of a urethral suppository according to the present invention showing multiple layers.

These multiple layers are shown in FIG. 17. The urethral suppository 124 is shown in cross section with three layers: a first layer 126 closest to the center of the suppository 124; a second intermediate layer 128; and a third layer 130 closest to the outside of the suppository 124. The urethral suppository 124 can be constructed with more or fewer layers.

Figure 18:
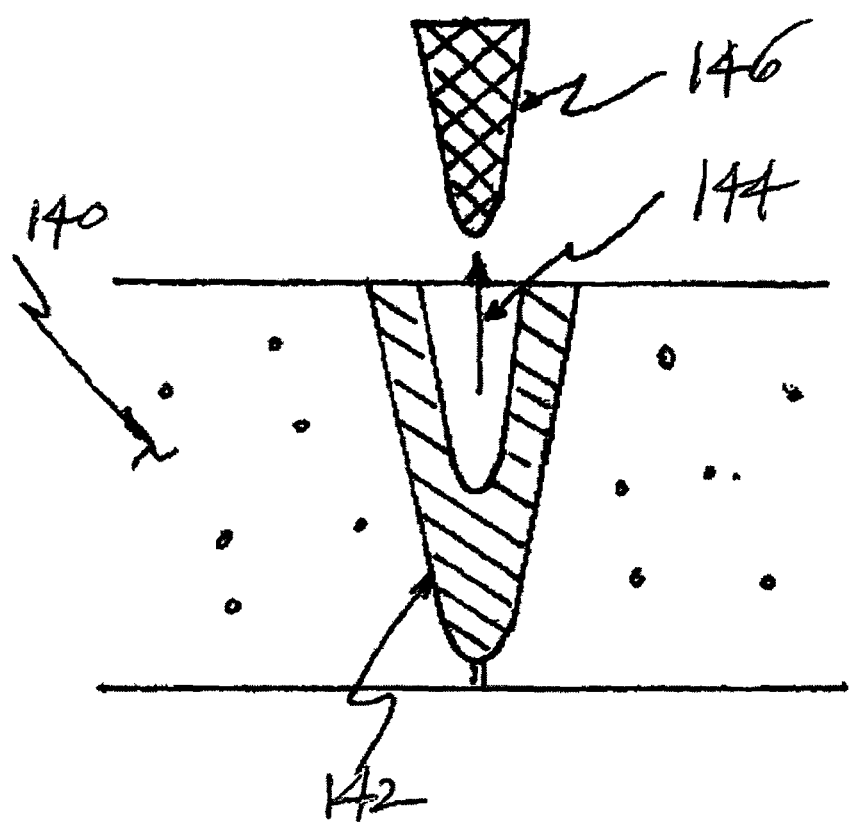
FIG. 18 is a schematic representation of a two-layer suppository according to the present invention showing inner space for suppository material created by insert.

FIG. 18 is a schematic representation of a two-layer suppository according to the present invention showing inner space for suppository material created by an insert. In FIG. 18, the suppository mold 140 for the outer layer of the suppository forms the space for the outer layer 142 of the suppository material, leaving an inner space 144 for the secondary (interior) layer of the suppository material. The inner space 144 for the secondary (interior) layer of the suppository material is created by an insert 146.

Figure 19:
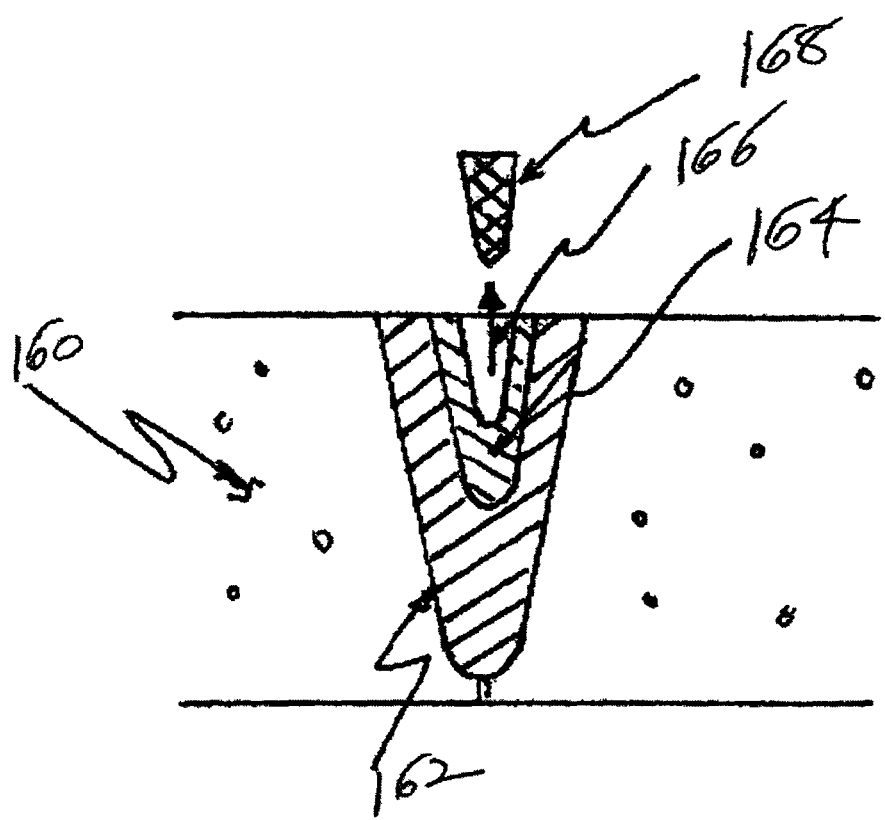
FIG. 19 is a schematic representation of a three-layer suppository according to the present invention showing inner space for suppository material created by insert.

FIG. 19 is a schematic representation of a three-layer suppository according to the present invention showing inner space for suppository material created by an insert. In FIG. 19, the suppository mold 160 for the outer layer of the suppository forms the space for the outer layer 162 of the suppository material. The inner layer 164 of the secondary suppository material is located inside the outer layer 162; the inner layer 164 is shaped to leave an inner space 166 for the tertiary suppository material. The inner space 166 for the tertiary suppository material is created by an insert 168.

Figure 20:
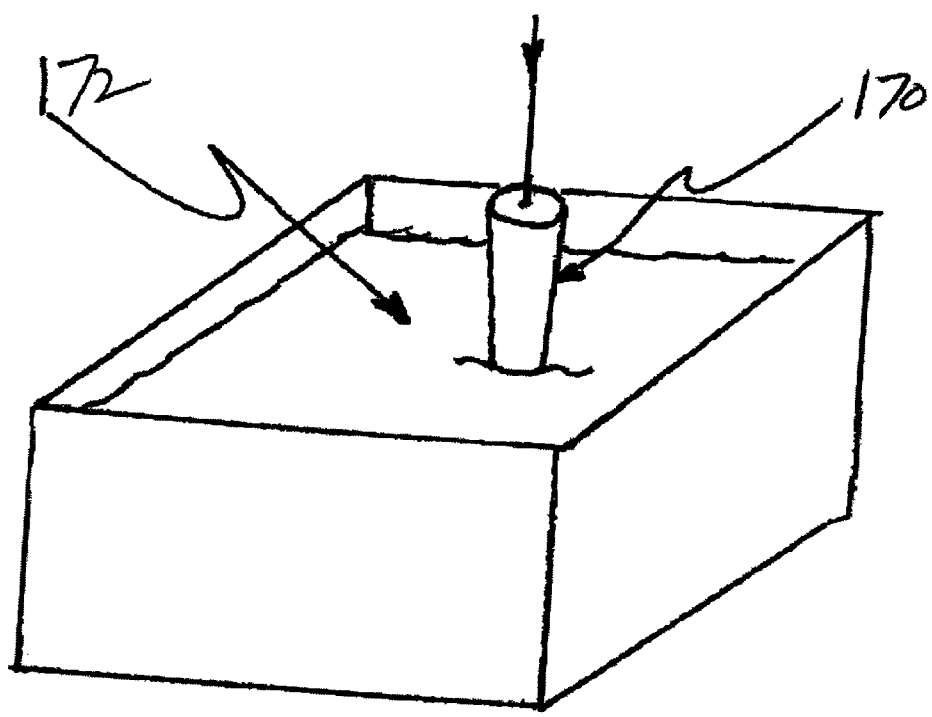
FIG. 20 is a perspective view of a suppository being dipped into a container of melted suppository material to create an outer layer of a multilayer suppository using a dipping process.

FIG. 20 is a perspective view of a suppository being dipped into a container of melted suppository material to create an outer layer of a multilayer suppository using a dipping process. The inner layer of the suppository 170 is dipped into a container 172 of melted suppository material to form the outer layer (not shown).

Figure 21:
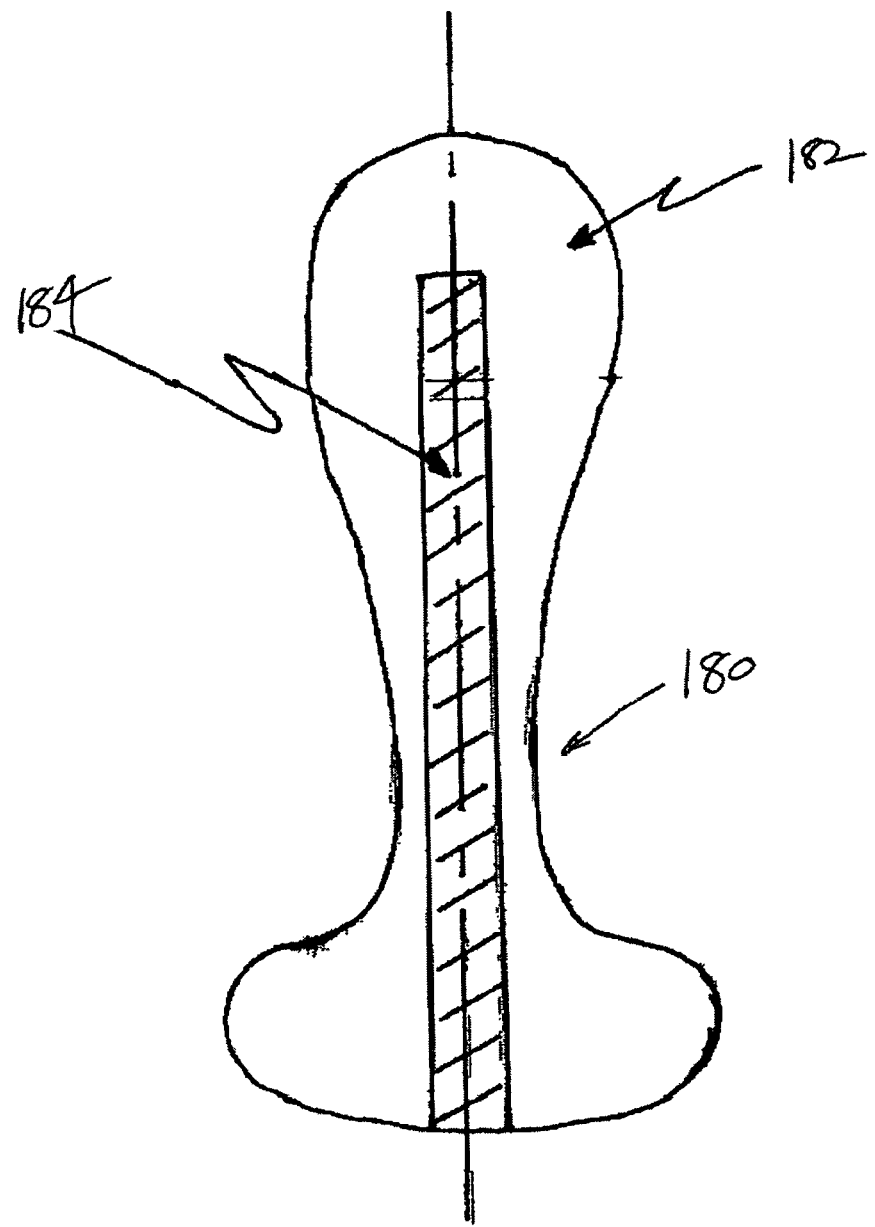
FIG. 21 is a representation of a multilayer suppository according to the present invention that employs different geometries in the layers.

FIG. 21 is a representation of a multilayer suppository employing different geometries (shapes) in the layers. In FIG. 21, the suppository 180 includes an outer primary layer 182 and an inner secondary layer 184. The outer primary layer 182 and the inner secondary later 184 have different geometries for optimal delivery of the therapeutic agent included in the suppository 180.

The present invention is not limited to urethral suppositories. The principles underlying the invention can also be used to construct a depot for luminal drug delivery. In general, a depot for luminal drug delivery according to the present invention comprises: (1) a carrier base material; (2) a therapeutic agent; and (3) a buffering agent, wherein the depot is formed into a solid structure configured for insertion into a body lumen of a patient.

The depot can have a substantially uniform composition. The depot can further comprise a polysaccharide such as a glycosaminoglycan as described above. The carrier base material can have a melting point such that the depot is substantially melted at body temperature. The therapeutic agent can be an anesthetic agent such as lidocaine, as described above. In one alternative, the carrier base material comprises a water soluble carrier base, as described above. In another alternative, the carrier base material comprises methyl butyl ketone, as described above; the carrier base material can further comprise paraffin to adjust the desired melting temperature.

The shape and dimensions of the depot can be determined by one of ordinary skill in the art with reference to the shape and dimensions of the lumen of the body into which the depot is intended to be inserted.

Another aspect of the present invention is a method for manufacturing a urethral suppository. In general, the method comprises the steps of:

(1) combining a therapeutic agent and a buffering agent in a liquid carrier base material until the therapeutic agent and the buffering agent have dissolved or been suspended in the liquid carrier base material; and (2) forming the liquid carrier base material, therapeutic agent, and buffering agent mixture into a suppository that is configured to be deployed within the urethra of a patient.

The method can further comprise combining a polysaccharide with the liquid carrier base material, as described above, to form a suppository including the polysaccharide. The polysaccharide can be selected from the group consisting of hyaluronic acid, hyaluronan, chondroitin sulfate, pentosan polysulfate, dermatan sulfates, heparin, heparan sulfates, keratan sulfates, dextran sulfates, and carrageenan as described above.

Typically, the step of forming the mixture into a suppository results in a finished suppository having a weight of from about 10 mg to about 1000 mg.

Typically, the therapeutic agent is an anesthetic agent as described above, such as lidocaine.

Typically, the quantity of buffering agent combined with the therapeutic agent in the liquid base material is sufficient to produce a pH of from about 7 to about 12 in the finished suppository.

Methods for manufacturing a urethral suppository that are within the scope of the present invention also include methods for manufacturing a multilayered suppository as described above. In general, such methods comprise the steps of:

(1) combining a therapeutic agent and a buffering agent in a liquid carrier base material until the therapeutic agent and the buffering agent have dissolved or been suspended in the liquid carrier base material; and (2) forming the liquid carrier base material, therapeutic agent, and buffering agent mixture into one or more layers of a multilayered suppository that is configured to be deployed within the urethra of a patient.

Another aspect of the present invention is a method of treating at least a portion of the urinary tract of a patient comprising the steps of:

(1) providing a urethral suppository according to the present invention as described above;

(2) deploying the urethral suppository within the patient's urethra; and (3) allowing the suppository to at least partially disintegrate and release the therapeutic agent and the buffering agent to treat at least a portion of the urinary tract of the patient.

In one alternative, disintegration of the suppository comprises melting of the carrier base material of the suppository. In another alternative, disintegration of the suppository comprises dissolving of the carrier base material of the suppository.

Typically, the therapeutic agent is an anesthetic agent, such as lidocaine, as described above. When the therapeutic agent is an anesthetic agent, in one alternative, treating at least a portion of the urinary tract of the patient comprises treatment of interstitial cystitis. Alternatively, treating at least a portion of the urinary tract of the patient comprises treatment of urethritis. When the therapeutic agent is an anesthetic agent, in another alternative, the urethral suppository is deployed within the urethra of the patient in order to desensitize the urethra prior to insertion of instrumentation into the urethra. When the therapeutic agent is an anesthetic agent, in still another alternative, treating at least a portion of the urinary tract of the patient comprises treatment of pain associated with the urethra or bladder.

In this method, the urethral suppository can further comprise a polysaccharide; the polysaccharide replaces or repairs the glycosaminoglycan barrier lining the urinary tract of the patient after insertion of the suppository into the urethra of the patient.

In methods according to the present invention, the exact formulation and dosage used in suppositories according to the present invention can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated, the general condition of the urinary tract, including the bladder and urethra, and the existence of other conditions affecting the urinary tract, such as infections, inflammation, or allergic reactions. The severity of the condition may, for example, be evaluated, in part, by standard prognostic evaluation methods. Further, the dose, and perhaps the dose frequency, will also vary according to the age, body weight, and response of the individual patient. A program comparable to that discussed above may be used in veterinary medicine.

Particularly when methods according to the present invention are used to treat interstitial cystitis, the method can further comprise the administration of an additional oral agent that acts to reduce abnormal permeability of bladder epithelium, so that the frequency of suppository use can be reduced according to the response of the patient. A suitable oral agent is pentosan polysulfate. Typically, when pentosan polysulfate is administered, the quantity used is from about 100 mg/day to about 600 mg/day; more typically, the quantity used is from about 100 mg/day to about 300 mg/day.

Particularly when methods according to the present invention are used to treat interstitial cystitis, the method can further comprise the administration of another agent such as a steroidal anti-inflammatory agent. Steroidal anti-inflammatory agents include, but are not limited to, alclometasone, amcinonide, beclomethasone, betamethasone, budesonide, clobetasol, clocortolone, hydrocortisone, cortisone, desonide, desoximetasone, dexamethasone, diflorasone, fludrocortisone, flunisolide, fluocinolone, fluocinonide, fluorometholone, flurandrenolide, halcinonide, medrysone, methylprednisolone, mometasone, prednisolone, prednisone, and triamcinolone, and their salt forms.

Again, particularly when methods according to the present invention are used to treat interstitial cystitis, the method can further comprise the administration of other pain agents in addition to the anesthetic agent administered via suppository, such as calcium T-type channel blockers which include, but are not limited to neurontin (gabapentin) and pregabalin; non-steroidal anti-inflammatory drugs (NSAIDs) which include, but are not limited to ketoprofen, ibuprofen, and ketorolac; or NMDA antagonists which include, but are not limited to ketamine.

The step of deploying the urethral suppository within the patient's urethra can further comprise use of a water-based lubricant. A certain fraction of patients who receive a suppository complain of burning in their urethra the first 2-4 minutes before the anesthetic agent takes effect. The anesthetic effect lasts 2-4 hours. The burning returns in these patients during their first void after the anesthetic wears off. Typically, these patients do not present, via PUF scores or patient history, as the most severe cases of IC. A solution to this problem is to coat the suppositories in a water-based lubricant prior to insertion. Three patients in the clinic, who had previously complained of burning a few hours after inserting a suppository, experienced no discomfort on insertion and no burning associated with voiding many hours after insertion (on the order of 2-8 hours).

There are two theories as to why this solution works. The first involves the hydrophilic nature of heparin acting almost as a desiccant in the suppository. By attracting water out of already fragile GAG layer due to disease, the heparin is exposing the interstitium to an even greater than usual potassium leak. The burning lessens and disappears after the first void as the heparin and the GAG layer become fully hydrated. The gel acts to hydrate the suppository and urethra, maintaining the GAG layer and preventing the potassium leak. The second is more mechanical in nature and involves irritation to the urethra as a result of the rubbing of the suppository on the urethra during insertion. These patients who experience post-suppository burning after voiding may have ultrasensitive urethras that react to the slightest physical contact. This contact may cause an immediate inflammatory response or a physical abrasion of the GAG. The gel in this situation acts as a lubricant that reduces the frictional contact between the urethra and suppository. Suitable lubricants include, but are not limited to, lubricants comprising water, glycerol, polyethylene glycol, and nontoxic preservatives such as parabens. This also applies to methods of treatment using multilayered suppositories according to the present invention as described below.

Methods of treatment according to the present invention also encompass methods of treatment using a multilayered suppository as described above. In general, such methods comprise the steps of:

(1) providing a multilayered urethral suppository according to the present invention as described above;

(2) deploying the multilayered urethral suppository within the patient's urethra; and (3) allowing the multilayered suppository to disintegrate and release the therapeutic agent and the buffering agent from at least one of the layers of the multilayered suppository to treat at least a portion of the urinary tract of the patient.

The invention is illustrated by the following Examples. These Examples are included for illustrative purposes only, and are not intended to limit the invention.

EXAMPLE 1

Suppository Fabrication

Animal tests, using a New Zealand White rabbit model, were conducted to determine the safety profile of buffered lidocaine absorption by measuring plasma levels of lidocaine in the systemic circulation using different carrier bases. Levels of lidocaine that would be toxic if injected intravenously were fabricated in a suppository carrier base. Different carrier bases were warmed in a 40° C. base and lidocaine was added in increments of 10% of the final weight of the mixture until it reached a ratio of 3:7 lidocaine to carrier base. The pH of the mixture was measured after all lidocaine had dissolved using a temperature compensating pH meter. A 30% lidocaine mixture was found to be the highest concentration lidocaine mixture achievable with the carrier base materials that were tried. The mixture was raised to 70° C. in a water bath and titrated with sodium bicarbonate to a pH of 8.5 while the mixture was gently stirred. Heating and stirring were stopped when the mixture lost its grainy appearance and became clear as all components dissolved in the carrier base. The mixture was drawn into tuberculin syringes, refrigerated overnight to form suppositories, and extruded the next day. The extruded suppositories were cut into thirds forming elongated sections having a length of about 2 cm and containing approximately 100 mg of lidocaine.

Urethral Insertion

Female New Zealand White rabbit subjects having a weight range of from about 3.5 kg to about 3.8 kg were anesthetized using intramuscular injections of ketamine and xylazine followed by half doses every hour as needed. The common carotid artery was exposed and cannulated to provide blood pressure measurements using a Life-Tech BP2110 pressure transducer and to draw blood. Another incision was made in the abdomen to expose the bladder. Through a small incision in the dome of the bladder, a 7 Fr pediatric feeding tube was placed in the bladder. All urine was drained from the bladder. The tube was fed out the bladder through the urethra and out the urethral opening. The suppositories were attached to lengths of 3-0 silk sutures that were fed through the tube and out the bladder incision. The tube was removed and the suture pulled through the incision, drawing the suppository into the urethra. The bladder incision was closed. Blood samples were drawn at 0, 15, 30, 60, and 90 minutes. After 90 minutes, the animals were sacrificed and their urethras removed and placed in a 10% formaldehyde solution for histological study.

Results

Free lidocaine was measured in plasma samples using the Abbott Laboratories TDx sheep albumin immunofluorescence assay. This assay is accurate for lidocaine levels from about 1-7 μg per ml of plasma. This assay was chosen for the reason that it is the standard means by which lidocaine concentration is measured for therapeutic purposes or in cases of suspected toxicity. In all carrier base mixtures, the maximum concentration of lidocaine in the blood was less than the resolution of the assay at 60 and 90 minutes after introduction. The maximum concentrations were observed between 15 and 30 minutes and did not exceed 1.1 μg of lidocaine per ml of plasma in all subjects. No subject had a measurable amount of lidocaine in its blood after 30 minutes. No significant hemodynamic changes were observed. The level of lidocaine administered to all subjects was a full order of magnitude greater than the currently prescribed clinical dose of analgesic lidocaine. Even at this elevated dose, the blood levels of lidocaine did not reach the threshold for a therapeutic effect (2-5 µg per ml) or toxic level (greater than 8 µg per ml). Histological examination of post-insertion urethras using hematoxylin/eosin (H & E) stain revealed an inflammatory response in epithelial cells lining the luminal urethra in subject receiving suppositories using a polyethylene glycol (PEG) carrier base. All other suppository carrier materials revealed normal cellular structure in the urethral cells.

No subject voided after insertion of the lidocaine urethral drug delivery mixture or after instillation of an alkalinized lidocaine solution. These results suggest that a buffered urethral delivery of lidocaine reduces patient exposure to toxic lidocaine levels, as evidenced by the low peak values of plasma lidocaine. In addition, the cessation of voiding after the administration of lidocaine implies that the drug is acting as a local anesthetic in the bladder and urethra. In such a case the amount of lidocaine transported into the tissue was sufficiently great to block nerve conduction and provide analgesia without exposing the subject to perilous plasma lidocaine concentrations.

EXAMPLE 2

Human clinical studies were conducted to determine the efficacy of a buffered lidocaine suppository having a mucopolysaccharide component to repair any defect or injury to a luminal surface of a patient's urethra. A conical suppository with a weight of approximately 500 mg was used in the study. Suppositories were fabricated to contain approximately 10% lidocaine buffered to a pH of about 7.8. Methyl butyl ketone (MBK) was chosen as the suppository carrier base material, because the melting time of the base material could be adjusted by addition of paraffin to a melting time within a range of 5-15 minutes. Suppositories were fabricated with PEG but without any active ingredient to determine if the inflammatory response observed in the animals resulted in any adverse effects in humans. Suppositories containing PEG carrier base materials were placed in two human subjects with both subjects complaining of urethral burning and urinary frequency. As a result, PEG was not used clinically in any further suppository formulation in these Examples. The suppository formulation used in the clinical study was as follows:

| Ingredient | Quantity |
| --- | --- |
| Therapeutic Agents | |
| Lidocaine | 45 mg |
| Heparin | 5000 units |
| Sodium Bicarbonate | 10 mg |
| Silica | 10 mg |
| Base Materials | |
| Methyl Butyl Ketone | 383 mg |
| Paraffin | 67 mg |

These carrier base materials were melted in a water bath at 60° C. and thoroughly mixed. The lidocaine, heparin, sodium bicarbonate, and silica were added to the carrier base materials while the mixture was gently stirred. After all suppository components were dissolved, the mixture was drawn into a syringe and injected into the cavities of the suppository mold. The mold was refrigerated overnight, after which the suppositories were removed from the mold and individually packaged. All suppositories were stored at 5° C. prior to use.

A total of 25 patients with a clinical diagnosis of IC with a urethral component determined by a score of greater than 15 out of 20 on a pain, urgency, and frequency (PUF) questionnaire received the buffered lidocaine suppositories. Patients were asked to grade their level of pain and discomfort pre- and post-insertion of the suppository. Before insertion of the suppository, patients graded their pain and discomfort at 8 on a 10 point analog pain scale with 10 being the highest degree of pain and discomfort and 0 being none. Patients graded their pain and discomfort 30 minutes after insertion of the suppository at 3 on the 10 point analog pain scale.

EXAMPLE 3

The study of Example 3 investigates the amount of sodium bicarbonate necessary to buffer a lidocaine solution to a pH of 7.6-7.8. Sodium bicarbonate in 3 mg increments was added to three concentrations of lidocaine in two volumes of water. The three concentrations of lidocaine were 30, 45, and 60 mg. The rationale for this choice of lidocaine concentrations was they represent a 5-12% range of lidocaine concentrations, by weight, in the 500 mg suppository expected to be used in future clinical studies. This range of lidocaine concentrations in the suppository covers what will most likely be the lidocaine concentration used in the final clinical version of a buffered lidocaine suppository.

To measure pH, the lidocaine and sodium bicarbonate must be dissolved in solution. However, lidocaine and sodium bicarbonate are not dissolved in the suppository. Rather, they are in suspension in the carrier base and dissolve only after they are released from the carrier base and exposed to an aqueous environment surrounding tissue. Because it is difficult or impossible to know how quickly the lidocaine/sodium bicarbonate is released and how much water is surrounding the suppository, we must understand how the pH of the lidocaine/sodium bicarbonate combination is affected by the amount of water in which the combination is dissolved. Two volumes of water, 5 and 10 ml, near the lower limits of fluid volumes required for measurement by the pH meter, were used to determine the effect of fluid volume on pH of the lidocaine/sodium bicarbonate mixture.

Figure 6:
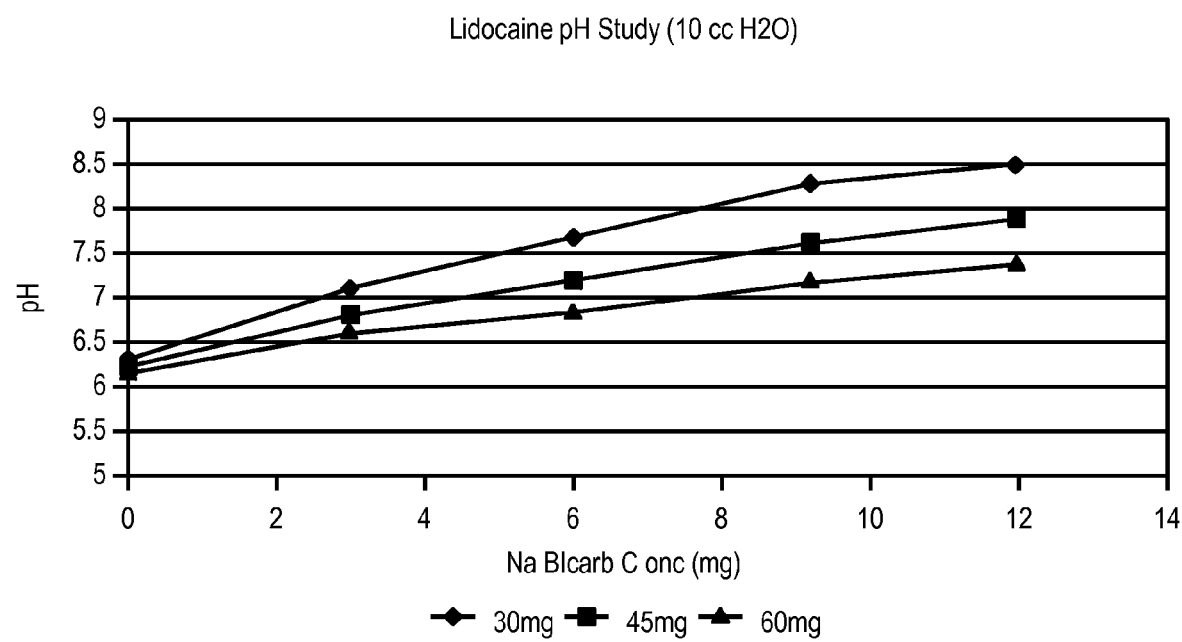
FIG. 6 is a graph showing the effect of lidocaine concentration on pH with the incremental addition of sodium bicarbonate to a fluid volume of 10 ml of water.
Figure 7:
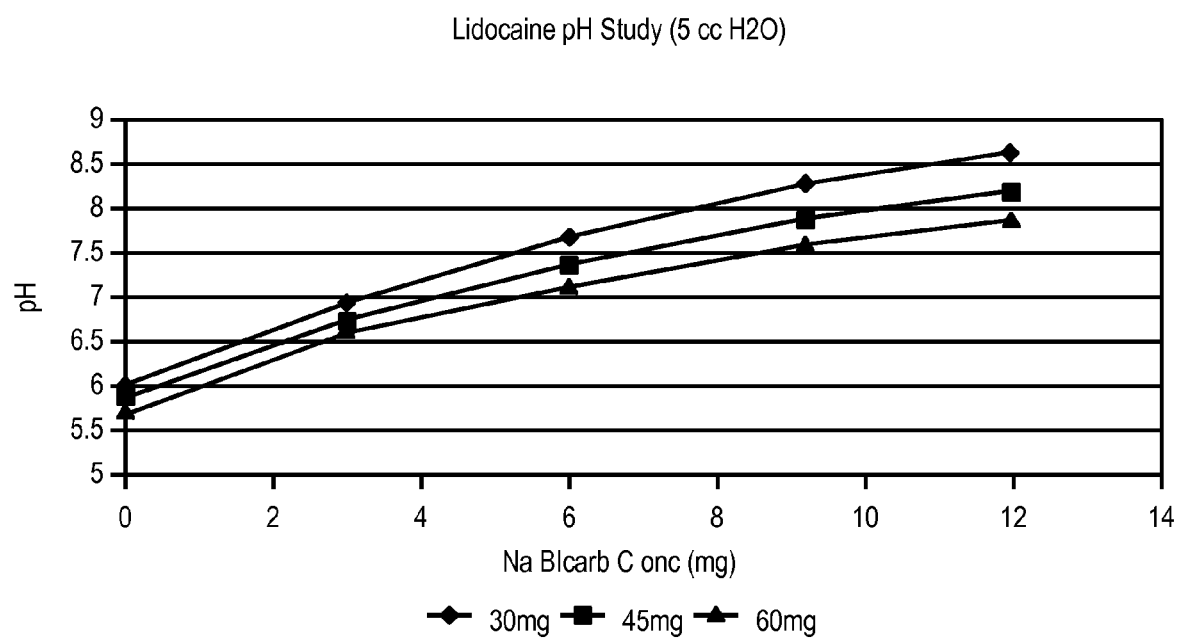
FIG. 7 is a graph showing the effect of lidocaine concentration on pH with the incremental addition of sodium bicarbonate to a fluid volume of 5 ml of water.
Figure 8:
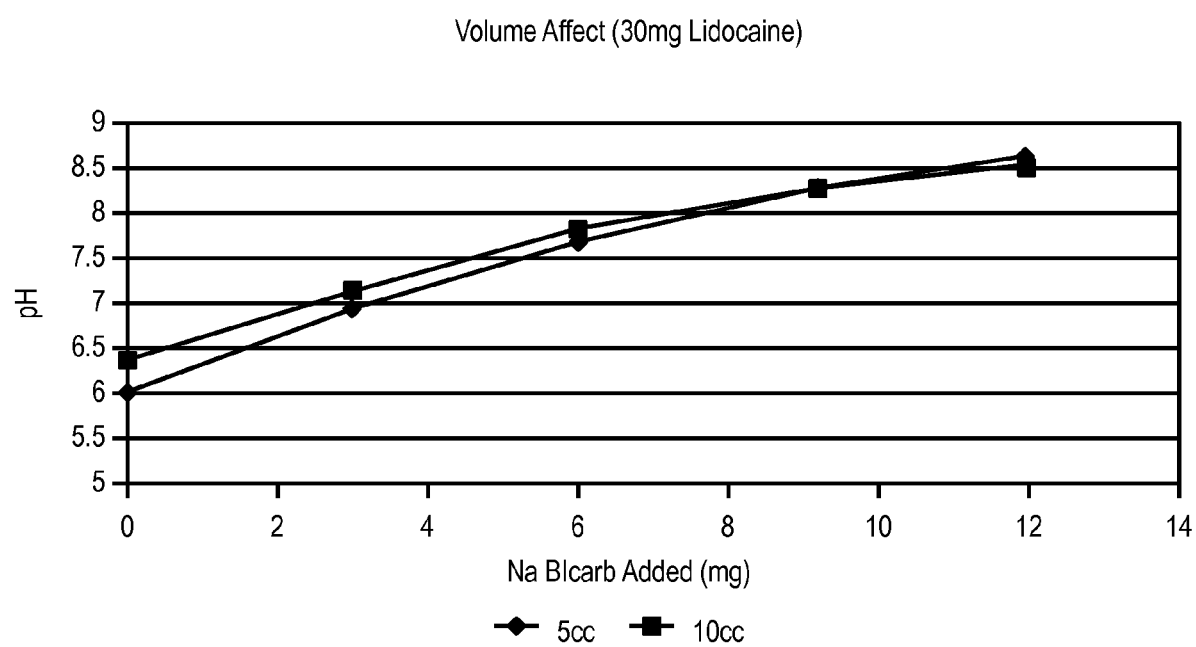
FIG. 8 is a graph showing the effect of fluid volume on pH with the addition of sodium bicarbonate to a solution containing 30 mg of lidocaine.
Figure 9:
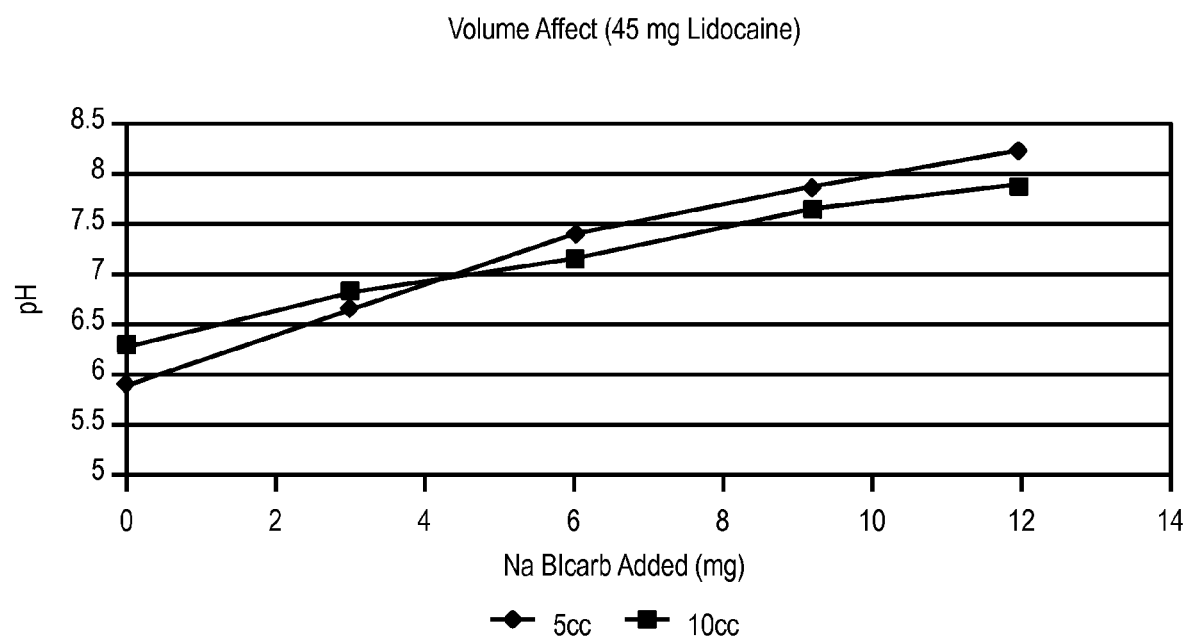
FIG. 9 is a graph showing the effect of fluid volume on pH with the addition of sodium bicarbonate to a solution containing 45 mg of lidocaine.
Figure 10:
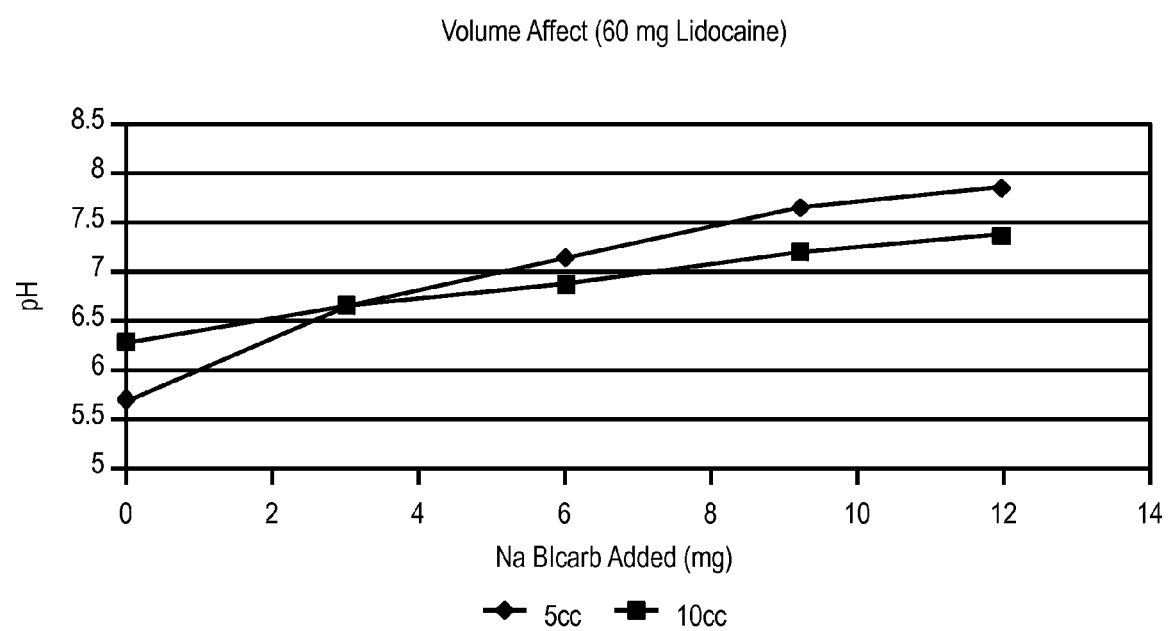
FIG. 10 is a graph showing the effect of fluid volume on pH with the addition of sodium bicarbonate to a solution containing 60 mg of lidocaine.

The study was conducted using an Omega PBH-45 pH meter. The lidocaine was dissolved in deionized water in a glass beaker. Sodium bicarbonate was added in increments of 3 mg, starting from 0 mg up to 12 mg. The pH was measured after each increment of sodium bicarbonate was thoroughly dissolved. Each study was repeated 4 times. The results of all studies are shown in FIGS. 6-10. In FIGS. 6 and 7, the effect of lidocaine concentration on pH was examined as sodium bicarbonate was incrementally added to two fluid volumes (10 ml for FIG. 6; 5 ml for FIG. 7). In FIGS. 8-10, the effect of fluid volume on pH was examined as sodium bicarbonate is added to three lidocaine solutions (30 ml for FIG. 8, 45 ml for FIG. 9, and 60 ml for FIG. 10).

The results of this study showed that a pH of 7.6-7.8 for a 5% or 10% buffered lidocaine suppository, approximately 550 mg total weight, is achieved with the use of approximately 5 mg and 10 mg, respectively, of sodium bicarbonate. Fluid volume does not appear to have a major effect on the relationship between lidocaine and sodium bicarbonate in determining the pH of the solution. Coupling this knowledge with a lack of understanding of the fluid volume into which the lidocaine/sodium bicarbonate mixture would be released from the suppository, our 5% and 10% lidocaine suppository formulations used the 5 mg and 10 mg sodium bicarbonate formulations, respectively.

EXAMPLE 4

The purpose of the study reported in Example 4 was to investigate the safety of placing a lidocaine suppository in the urethra. Lidocaine suppositories containing an ×5 clinical lidocaine dose were used in a rabbit model. Clinical safety was determined by measuring plasma lidocaine levels as a result of absorption of lidocaine in the urethra, through tissue, and into the systemic circulation. Plasma lidocaine levels were measured using a TDx/TDxFLx free lidocaine assay. The plasma level of lidocaine considered to be clinically toxic is 6-8 µg/ml of plasma. For comparative purposes, a parallel study was conducted to investigate the safety of a similar dose of lidocaine injected directly into the bladder.

The lidocaine suppositories were fabricated by dissolving lidocaine buffered with sodium bicarbonate to a pH of 8 in a glycerinated gelatin base at 70° C. The suppositories were drawn into a tuberculin syringe and formed into cylindrical shapes with a final concentration of approximately 100 mg of lidocaine/suppository. A 3-0 silk suture was drawn through the axis of the suppository to aid in the positioning of the suppository in the rabbit urethra.

Female New Zealand White rabbits, 3.5-4 Kg, were anesthetized using a mixture of ketamine and xylazine. A cannula was placed in the right carotid artery to obtain blood samples and monitor arterial pressure during the entire procedure. A 6 Fr Foley catheter was placed through the urethra via a suprapubic bladder route. The suture was fed through the catheter and out the suprapubic access site. The catheter was then removed and the suture was drawn out of the bladder as to position the suppository in the middle urethra. For intravesical instillation, a 6 Fr catheter was placed transurethrally in the bladder and all urine drained. A 5 ml solution of 100 mg of lidocaine was then instilled in the bladder through the catheter. Plasma samples were drawn through the carotid cannula at 0, 15, 30, 60, 90, and 120 minutes.

Figure 11:
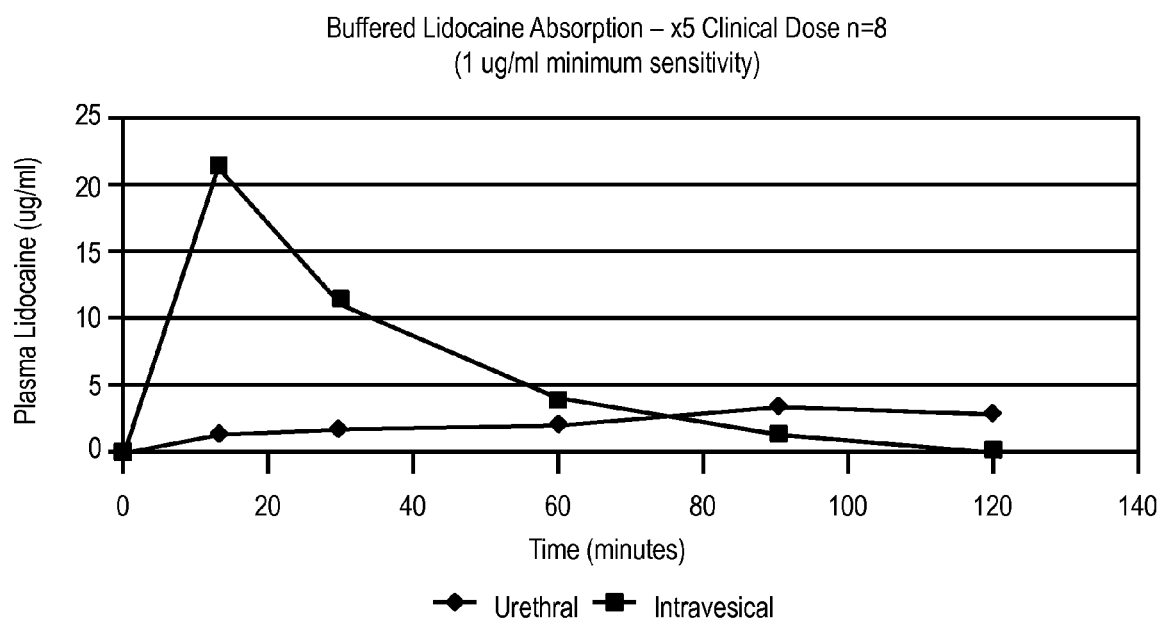
FIG. 11 is a graph showing the results of lidocaine absorption as a result of intravesical instillation and as a result of urethral suppository administration with plasma lidocaine concentration plotted against time, with a 100 mg dose administered both intravesically and by suppository.
Figure 12:
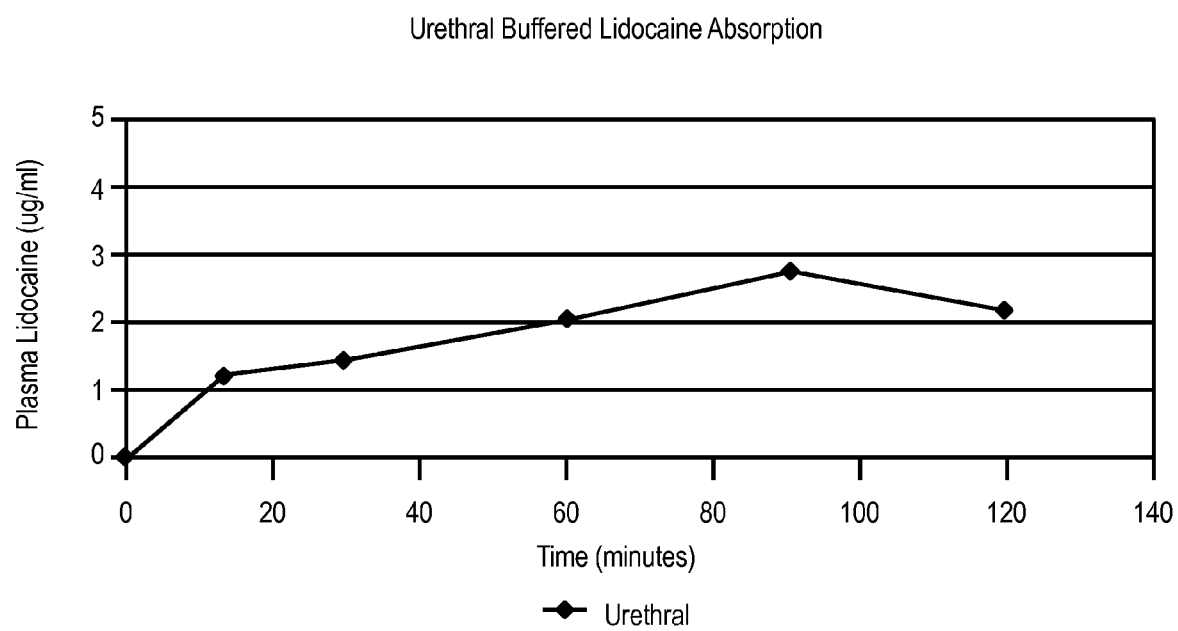
FIG. 12 is a graph showing the data of FIG. 11 for urethral suppository administration of lidocaine replotted on a different scale.
Figure 13:
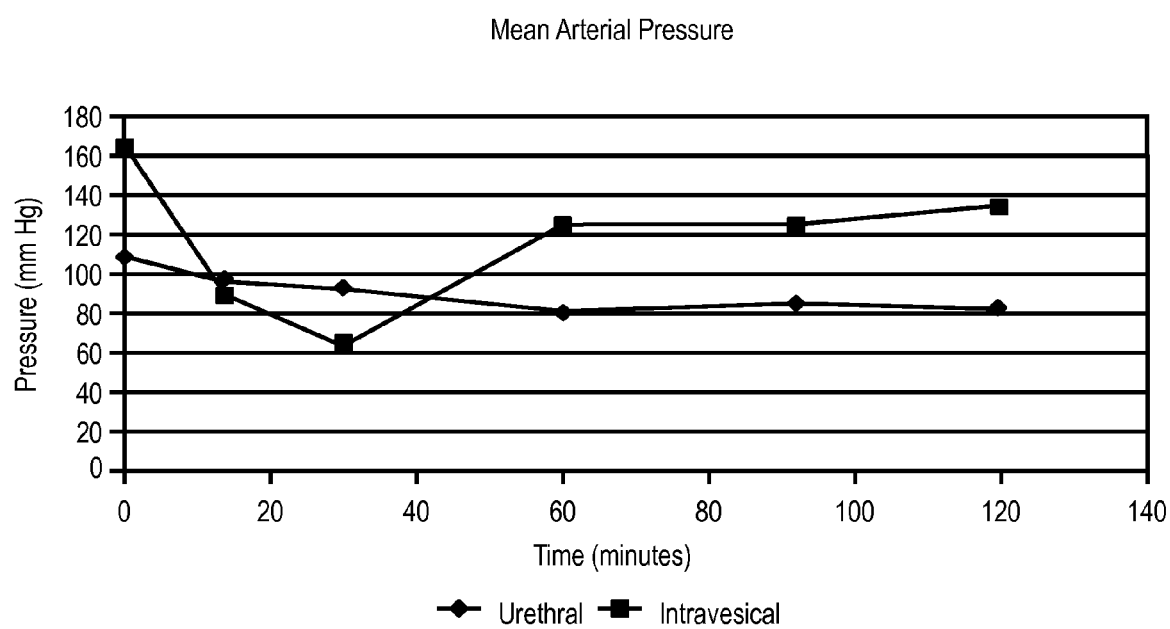
FIG. 13 is a graph showing the mean arterial blood pressure (MAP) after urethral and suppository lidocaine administration.

The results of the lidocaine absorption are shown in FIG. 11. Plasma levels of urethral lidocaine were less than 10% of intravesical lidocaine for all sample times. Intravesical lidocaine absorption showed a rapid rise to a peak level of over 35 µg/ml, then a fast decline to 5 µg/ml in 60 minutes. In contrast, urethral absorption of lidocaine never rose above 1 µg/ml and remained relatively steady for the entire measurement period; see FIG. 12. Urethral absorption did not cause significant hemodynamic changes as reflected in the mean arterial pressure (MAP), shown in FIG. 13.

Lidocaine absorption is much less through the urethra than the bladder at the same dose, 100 mg for the current study. The maximum recommended adult dose of lidocaine hydrochloride is 4.5 mg/Kg (PDR 1997. p. 564). The current rabbit study used 100 mg/4 Kg=25 mg/Kg, more than five times the maximum dose used in humans. Urethral absorption, even at an ×5 maximum dose, remained below plasma levels considered toxic. Additionally, the level of plasma lidocaine from urethral absorption maintained a steady level for the entire measurement period in contrast to the rapid rise then decline of plasma lidocaine levels from intravesical absorption.

EXAMPLE 5

Figure 14:
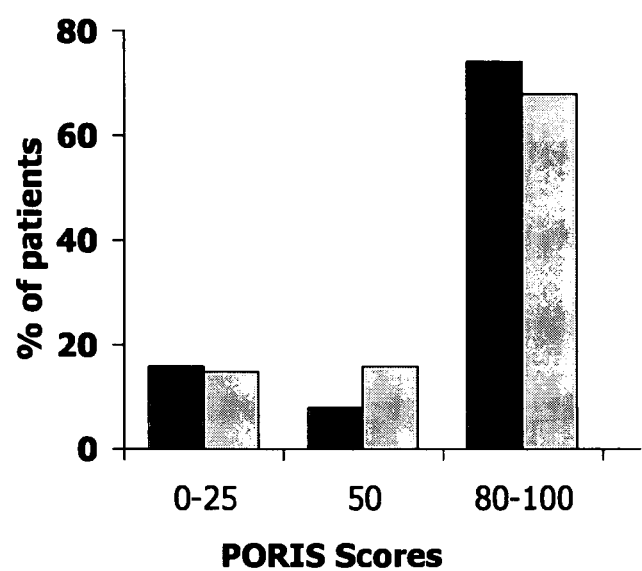
FIG. 14 is a graph showing % of patients experiencing improvement in their symptoms of pain (red, n=24) or urgency (yellow, n=19) as rated by a PORIS questionnaire 30 minutes after having a suppository with 10 mg lidocaine, 5000 units heparin, with buffer and base.

The purpose of the study reported in Example 5 was to investigate how effective were lower amounts of lidocaine in the urethral suppository. In this case, a suppository was made in which the lidocaine amount was reduced to 10 mg. All other components in the suppository were kept constant. Patients with a urethral component to their interstitial cystitis had a suppository emplaced in their urethra and after 30 minutes were asked to rate their urethral component of their pain and urgency by filling out a PORIS questionnaire (patient overall rating of symptom improvement) at 30 minutes. As can be seen in FIG. 14, the vast majority of patients (>80%) had significantly improved symptoms as defined by ≥50% symptom improvement of pain (n=24) or urgency (n=19) from their urethra.

EXAMPLE 6

Figure 15:
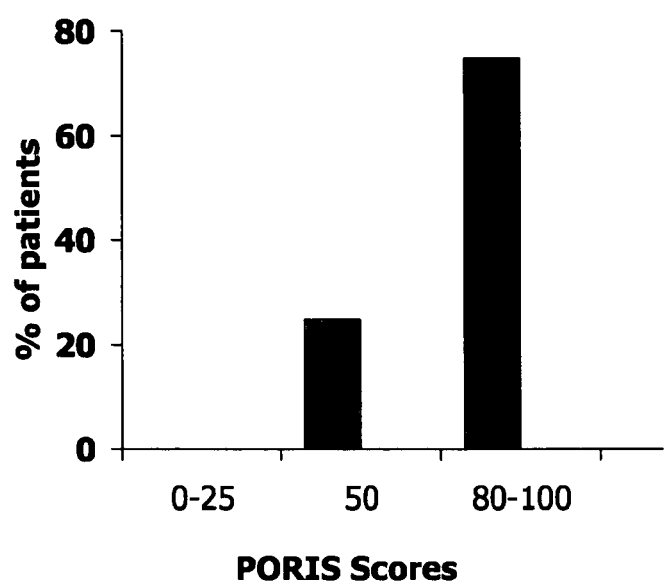
FIG. 15 is a graph showing % of patients experiencing improvement in their symptoms of pain (n=4) as rated by a PORIS questionnaire 30 minutes after having a suppository with 10 mg lidocaine, 5000 units heparin with THAM (tris) buffer in place of bicarbonate and base.

The purpose of the study reported in Example 6 was to investigate an alternative buffer to sodium bicarbonate in the suppository. Tham (Tris) was used in the suppository as the buffer and the remaining components were kept the same (10 mg lidocaine and 5,000 units heparin). Patients with a urethral component to their interstitial cystitis had a suppository emplaced in their urethra and after 30 minutes were asked to rate their urethral component of their pain and urgency by filling out a PORIS questionnaire (patient overall rating of symptom improvement) at 30 minutes. As can be seen in FIG. 15, all patients experienced a ≥50% or more symptom improvement of pain (n=4) from their urethra. Consequently, this experiment demonstrated that alternative buffers other than sodium bicarbonate can be used in the suppository.

EXAMPLE 7

Figure 16:
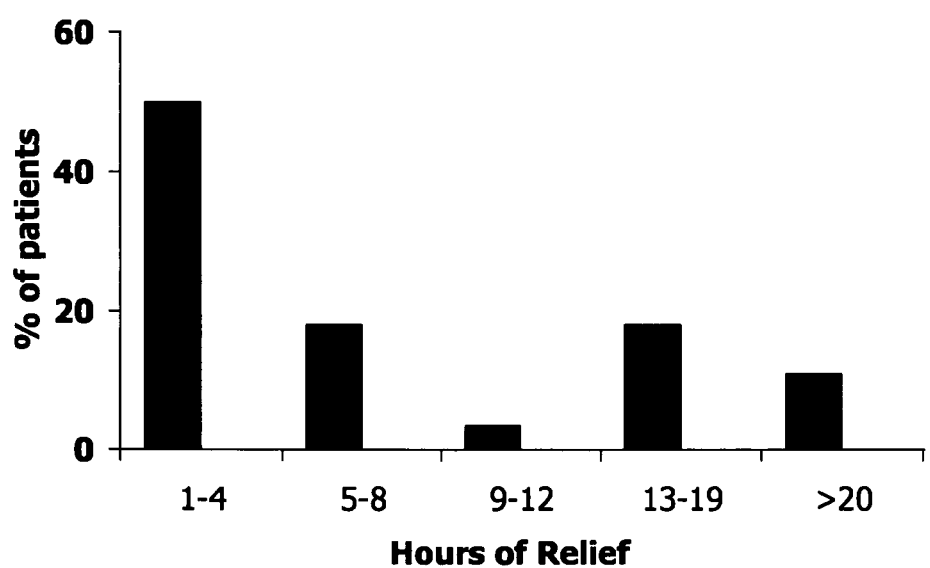
FIG. 16 is a graph showing duration of pain relief of % of patients over time when contacted 24 hours after the initial treatment (n=33). The median duration of relief was 4 hours.

The purpose of the study reported in Example 7 was to investigate the duration of relief from pain upon treatment with the urethral suppository. Subjects that had received the urethral suppository with 10 mg lidocaine with the 5000 units heparin and sodium bicarbonate were followed up after 24 hours and asked when their relief from pain ended. The median duration of relief was 4 hours. However, patients experienced pain relief from ranging from 1 hour to 24 hours. The percentage of patients experiencing pain relief in various time groups is shown in FIG. 16. In light of the fact that lidocaine half life is quite short, the existence of patients with responses longer than 4 hours implies that the heparin contributes to the longevity of the pain relief of the suppository.

Advantages of the Invention

Suppositories according to the present invention provide an effective and simple means for treatment of a number of serious urinary tract conditions, including interstitial cystitis. They are well tolerated and can be utilized by most patients. They provide rapid relief and can be used together with other treatments, including oral administration of agents such as sodium pentosanpolysulfate (Elmiron®). When suppositories according to the present invention are administered, they provide an efficient means of delivering an anesthetic agent such as lidocaine to tissues of the urinary tract without risking the possibility of excessive systemic doses of the anesthetic agent.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of ordinary skill in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A urethral suppository comprising:
   (a) a carrier base material;
   (b) a therapeutic agent; and
   (c) a buffering agent;
   wherein the suppository is formed into a solid structure configured for insertion into the urethra of a patient; and
   wherein the carrier base material comprises methyl butyl ketone (MBK) wax base.

2. The urethral suppository of claim 1 wherein the suppository has a substantially uniform composition.

3. The urethral suppository of claim 1 wherein the carrier base material has a melting point such that the suppository is substantially melted at body temperature.

4. The urethral suppository of claim 1 wherein the carrier base material is a water soluble carrier base.

5. The urethral suppository of claim 1, wherein the carrier base material comprises MBK wax base and paraffin.

6. The urethral suppository of claim 1 wherein the therapeutic agent is an anesthetic agent.

7. The urethral suppository of claim 6 wherein the anesthetic agent is present in a quantity sufficient to prevent or ameliorate a urinary tract disorder.

8. The urethral suppository of claim 7 wherein the urinary tract disorder is interstitial cystitis.

9. The urethral suppository of claim 6 wherein the anesthetic agent is at least one anesthetic agent selected from the group consisting of lidocaine, benzocaine, bupivacaine, articaine, cocaine, etidocaine, flecainide, mepivacaine, pramoxine, prilocaine, procaine, chloroprocaine, oxyprocaine, proparacaine, ropivacaine, tetracaine, dyclonine, dibucaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof, and combinations thereof.

10. The urethral suppository of claim 9 wherein the anesthetic agent is at least one anesthetic agent selected from the group consisting of lidocaine, prilocaine, benzocaine, mepivacaine, etidocaine, articaine, bupivacaine, procaine, and tetracaine.

11. The urethral suppository of claim 10 wherein the anesthetic agent is lidocaine.

12. The urethral suppository of claim 1 wherein the buffering agent is present in a quantity such that the buffering agent buffers the suppository at a pH that ensures that a sufficient portion of an anesthetic agent that is present in the suppository is present in an uncharged state so that the anesthetic agent can cross cell membranes of cells surrounding the urethra.

13. The urethral suppository of claim 12 wherein the buffering agent maintains the pH of the suppository in a range of from about 7 to about 12.

14. The urethral suppository of claim 13 wherein the buffering agent maintains the pH of the suppository in a range of from about 7 to about 9.

15. The urethral suppository of claim 1 wherein the buffering agent is at least one buffer selected from the group consisting of sodium bicarbonate buffer, calcium bicarbonate buffer, tris(hydroxymethyl)aminomethane (Tris or THAM), MOPS (3-(N-morpholino)propanesulfonic acid) buffer, HEPES (N-(2-hydroxyethyl)piperazine-N'-(2-ethanesulfonic acid) buffer, ACES (2-[(2-amino-2-oxoethyl)amino]ethanoesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS (N-(2-hydroxyethylpiperazine)-N'-(3-propanesulfonic acid), buffer, HEPPSO (N-{2-hydroxyethyl}piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropaneulfonic acid) buffer; TAPS (N-tris[hydroxymethyl)methyl-3-aminopropanesulfonic acid) buffer, TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer, and combinations thereof 16. The urethral suppository of claim 15 wherein the buffering agent is selected from the group consisting of sodium bicarbonate buffer and tris(hydroxymethyl)aminomethane buffer.

17. The urethral suppository of claim 16 wherein the buffering agent is sodium bicarbonate buffer.

18. The urethral suppository of claim 1 further comprising a polysaccharide.

19. The urethral suppository of claim 18 wherein the polysaccharide is present in the suppository in a sufficient quantity to prevent or ameliorate a urinary tract disorder.

20. The urethral suppository of claim 19 wherein the urinary tract disorder is interstitial cystitis.

21. The urethral suppository of claim 18 wherein the polysaccharide is at least one polysaccharide selected from the group consisting of hyaluronic acid, hyaluronan, chondroitin sulfate, pentosan polysulfate, dermatan sulfates, heparin, heparan sulfates, keratan sulfates, dextran sulfates, and carrageenan.

22. The urethral suppository of claim 21 wherein the polysaccharide is heparin.

23. The urethral suppository of claim 1 wherein the suppository is from about 10 mg to about 1000 mg in weight.

24. The urethral suppository of claim 23 wherein the suppository is from about 400 mg to about 600 mg in weight.

25. The urethral suppository of claim 1 wherein the therapeutic agent is an anesthetic agent, and wherein the suppository comprises from about 1 mg to about 100 mg of anesthetic agent.

26. The urethral suppository of claim 25 wherein the suppository comprises from about 30 mg to about 60 mg of anesthetic agent.

27. The urethral suppository of claim 1 wherein the suppository comprises from about 0.5 mg to about 100 mg of buffering agent.

28. The urethral suppository of claim 27 wherein the suppository comprises from about 1 mg to about 20 mg of buffering agent.

29. A urethral suppository comprising:
(a) a carrier base material;
(b) a therapeutic agent; and
(c) a buffering agent;
wherein the suppository is formed into a solid structure configured for insertion into the urethra of a patient;
wherein the suppository is in a configuration selected from the group consisting of a cylinder, a cone, and an ellipsoid; and
wherein the carrier base material comprises methyl butyl ketone (MBK) wax base.

30. A urethral suppository comprising:
(a) a carrier base material;
(b) a therapeutic agent; and
(c) a buffering agent;
wherein the suppository is formed into a solid structure configured for insertion into the urethra of a patient;
wherein the suppository is elongated structure with a transverse dimension of from about 1 mm to about 10 mm; and
wherein the carrier base material comprises methyl butyl ketone (MBK) wax base.

31. The urethral suppository of claim 30 wherein the suppository is an elongated structure with a transverse dimension of from about 3 mm to about 6 mm.

32. A urethral suppository comprising:
(a) a carrier base material;
(b) a therapeutic agent; and
(c) a buffering agent;
wherein the suppository is formed into a solid structure configured for insertion into the urethra of a patient;
wherein the suppository is an elongated structure with a length of from about 5 mm to about 50 mm; and
wherein the carrier base material comprises methyl butyl ketone (MBK) wax base.

33. The urethral suppository of claim 32 wherein the suppository is an elongated structure with a length of from about 15 mm to about 35 mm.

34. The urethral suppository of claim 1 wherein the suppository comprises a quantity of buffering agent that comprises from about 1 percent to about 30 percent by weight of the overall weight of the suppository.

35. The urethral suppository of claim 1 further comprising a quantity of a suspending agent sufficient to prevent active ingredients within the suppository from aggregating.

36. The urethral suppository of claim 35 wherein the suspending agent is silica.

\* \* \* \* \*